(12) United States Patent
Kujak et al.

(10) Patent No.: US 10,969,148 B2
(45) Date of Patent: Apr. 6, 2021

(54) SYSTEM AND METHOD FOR DETECTING REFRIGERANT CONTAMINATION IN AN HVACR SYSTEM

(71) Applicant: TRANE INTERNATIONAL INC., Davidson, NC (US)

(72) Inventors: Stephen Anthony Kujak, Brownsville, MN (US); Julie Ann Majurin, Mindoro, WI (US); Randal Newton, St. Paul, MN (US); Kenneth J. Schultz, Onalaska, WI (US)

(73) Assignee: TRANE INTERNATIONAL INC., Davidson, NC (US)

( * ) Notice: Subject to any disclaimer, the term of this patent is extended or adjusted under 35 U.S.C. 154(b) by 214 days.

(21) Appl. No.: 15/714,620

(22) Filed: Sep. 25, 2017

(65) Prior Publication Data

US 2018/0087815 A1 Mar. 29, 2018

Related U.S. Application Data

(60) Provisional application No. 62/399,070, filed on Sep. 23, 2016.

(51) Int. Cl.
| | | |
|---|---|---|
| *G01N 29/024* | (2006.01) | |
| *F25B 49/00* | (2006.01) | |
| *G01N 33/00* | (2006.01) | |
| *G01N 25/18* | (2006.01) | |
| G01N 30/66 | (2006.01) | |

(52) U.S. Cl.
CPC ......... *F25B 49/005* (2013.01); *G01N 25/18* (2013.01); *G01N 29/024* (2013.01); *G01N 33/0032* (2013.01); *F25B 2400/12* (2013.01); *F25B 2400/121* (2013.01); *F25B 2500/06* (2013.01); *G01N 30/66* (2013.01); *G01N 2291/011* (2013.01); *G01N 2291/021* (2013.01)

(58) Field of Classification Search
CPC ............... F25B 49/005; F25B 2400/12; F25B 2400/121; F25B 2500/06; G01N 25/18; G01N 29/024; G01N 2291/011; G01N 2291/021; G01N 33/0032; G01N 30/66
See application file for complete search history.

(56) References Cited

U.S. PATENT DOCUMENTS

| | | |
|---|---|---|
| 2,863,299 A | 12/1958 | Ammons |
| 3,084,658 A | 4/1963 | Schell |
| 3,288,960 A | 11/1966 | Miller |
| | (Continued) | |

*Primary Examiner* — Suman K Nath
(74) *Attorney, Agent, or Firm* — Hamre, Schumann, Mueller & Larson, P.C.

(57) ABSTRACT

A system for detecting if a refrigerant in an HVACR system is contaminated. The system includes a detector that detectes a property of a refrigerant gas in a vapor space and compares the detected property with a reference property for uncontaminated refrigerant gas. The detector determines that a contaminant is present in the refrigerant gas if the detected property is different from the reference property. The property detected by the dectector can be either a speed of sound through the refrigerant gas or a thermal conductivity of the refrigerant gas. Also disclosed is a method for detecting contamination of refrigerant gas in a HVACR system that includes detecting, by a detector, a property of refrigerant gas in a vapor space of the HVACR system.

15 Claims, 10 Drawing Sheets

(56) References Cited

U.S. PATENT DOCUMENTS

| | | |
|---|---|---|
| 3,846,730 A | 11/1974 | Hamilton |
| 3,959,980 A | 6/1976 | Hamilton |
| 4,090,371 A | 5/1978 | Keane |
| 4,449,396 A | 5/1984 | Bzdula |
| 4,498,305 A | 2/1985 | Bzdula |
| 4,551,984 A | 11/1985 | Vogel et al. |
| 4,823,625 A | 4/1989 | Hamilton |
| 4,890,459 A | 1/1990 | Havemann |
| 4,970,891 A | 11/1990 | Blevins et al. |
| 5,071,768 A | 12/1991 | Klodowski |
| 5,127,433 A | 7/1992 | Argyle et al. |
| 5,158,747 A | 10/1992 | Manz et al. |
| 5,161,385 A | 11/1992 | Schumacher |
| 5,237,873 A | 8/1993 | Eichenlaub |
| 5,295,360 A | 3/1994 | Olds et al. |
| 5,363,661 A | 11/1994 | Condit et al. |
| 5,377,496 A | 1/1995 | Otto et al. |
| 5,383,338 A | 1/1995 | Bowsky et al. |
| 5,419,177 A | 5/1995 | Pastorello |
| 5,439,644 A | 8/1995 | Gramkow et al. |
| 5,514,595 A | 5/1996 | Olds et al. |
| 5,524,477 A | 6/1996 | Wajid |
| 5,528,924 A | 6/1996 | Wajid et al. |
| 5,575,833 A | 11/1996 | Griffin |
| 5,846,833 A | 12/1998 | Clough et al. |
| 6,514,765 B1 | 2/2003 | Scaringe et al. |
| 6,576,473 B1 | 6/2003 | Scaringe et al. |
| 7,043,969 B2 | 5/2006 | Matsiev et al. |
| 7,082,774 B2 | 8/2006 | Ayub |
| 7,350,367 B2 | 4/2008 | Matsiev et al. |
| 7,721,590 B2 | 5/2010 | Kolosov et al. |
| 8,058,070 B2 | 11/2011 | Minor et al. |
| 8,070,355 B2 | 12/2011 | Minor et al. |
| 2005/0076704 A1* | 4/2005 | Wu .................. G01N 15/06 73/24.03 |
| 2011/0259039 A1* | 10/2011 | Ma .................. F25B 15/02 62/495 |
| 2012/0228050 A1* | 9/2012 | Bulat .................. F01N 1/023 181/213 |
| 2013/0213114 A1 | 8/2013 | Wetzig et al. |
| 2017/0160126 A1* | 6/2017 | Pfeiffer ............ G01N 29/024 |
| 2018/0017519 A1* | 1/2018 | Chen .................. F25B 49/00 |

* cited by examiner

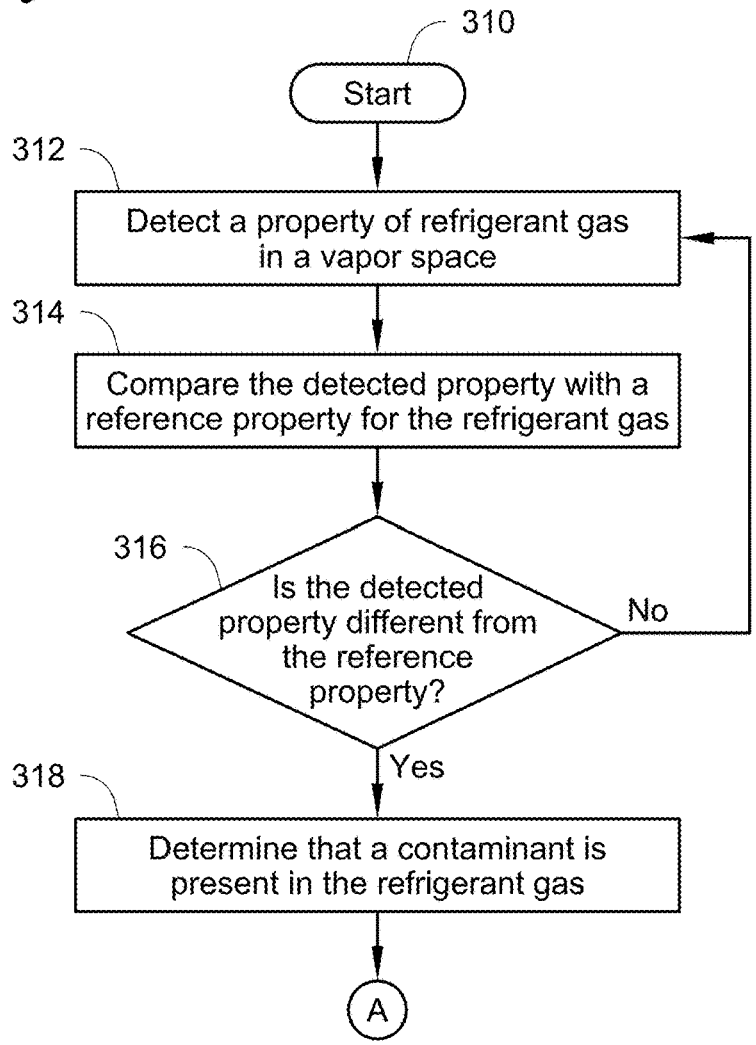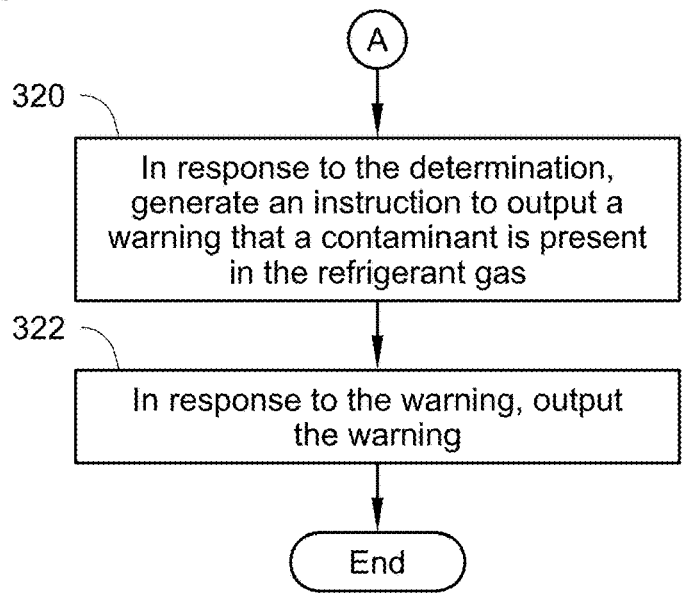

SYSTEM AND METHOD FOR DETECTING REFRIGERANT CONTAMINATION IN AN HVACR SYSTEM

FIELD

The disclosure herein relates generally to heating, ventilation, air-conditioning and refrigeration ("HVACR") systems and methods, and more particularly to contamination detection of refrigerant used in the HVACR systems and methods.

BACKGROUND

HVACR systems generally use a refrigerant for cooling, heating or dehumidifying a heat transfer medium. A refrigerant for an HVACR system includes, but are not limited to, HCFC, HFC, HCFO or HFO refrigerants or blends of these refrigerants. When the refrigerant is contaminated or counterfeited with material other than the refrigerant to be used for the HVACR system, the HVACR system will fail to operate adequately. Even worse, the HVACR system could be susceptible to damage or explosion if the contaminant or counterfeiting refrigerant, for example, methyl chloride (R-40), has a high toxicity or flammability potential.

SUMMARY

The embodiments described herein relate to systems or methods for detecting contamination of refrigerant in a heating, ventilation, air-conditioning and refrigeration ("HVACR") unit.

In some embodiments, there is provided a system for detecting contamination of refrigerant gas in an HVACR system that includes: a vapor space containing refrigerant gas; and a detector, connected to the vapor space, detecting a property of the refrigerant gas in the vapor space, comparing the detected property with a reference property for an uncontaminated refrigerant gas to be used for the HVACR system, and determining that a contaminant is present in the refrigerant gas of the vapor space if the detected property is different from the reference property. In some embodiments, if a difference between the detected property and the reference property is greater than a predetermined threshold, the detected property is determined as different from the reference property. In some embodiments, the vapor space is a refrigerant reservoir or volume inside a component in a heat transfer circuit of the HVACR system, a fluid line included in a heat transfer circuit of the HVACR system, or a refrigerant container in communication with the heat transfer circuit.

In some embodiments, the system may further include a controller, in communication with the detector, receiving the determination that a contaminant is present in the refrigerant gas of the vapor space from the detector and generating an instruction to output the warning of the presence of contamination; and an output device, in communication with the controller, outputting a warning that a contaminant is present in the refrigerant gas of the vapor space, in response to receiving the instruction from the controller.

In some embodiments, the property of refrigerant gas is a color of the reagent when the refrigerant gas from the vapor space passes the reagent. The reagent reacts with potential contaminants and thereby has a change of color while the reagent does not react by changing color to an uncontaminated refrigerant gas to be used for the HVACR system. In some embodiments, the detector may include an internal sensor that assesses a hue and value of the detected color of the reagent, compares the levels of hue and value of the detected color with the levels of hue and value of the reference, and determines that a contaminant is present in the refrigerant gas of the vapor space if the levels of hue and value of the detected color are different from the levels of hue and value of the reference color. In some embodiments, if differences between the levels of hue and value of the detected color and the levels of hue and value of the reference color are greater than predetermined threshold(s), the detected color is determined as different from the reference color. In some embodiments, the reagent may be sodium chromate or sodium permanganate. In some embodiments, the detector may include a sight glass through which the color change of the reagent may be observed. In some embodiments, the detector further includes an indicator that indicates reference color of the reagent for the uncontaminated refrigerant gas to be used for the HVACR system.

In some embodiments, the property of refrigerant gas is a speed of sound through the refrigerant gas. The speed of sound may be given by a relationship, $$v = \sqrt{\frac{\gamma RT}{M}},$$

in which v is the speed of sound through the refrigerant gas, γ is an adiabatic constant, R is a gas constant, M is a molecular weight of the refrigerant gas, and T is an absolute temperature. In some embodiments, the detector may include a transducer outputting sound waves, a receiver receiving the sound waves that are transmitted or reflected, and a sensor sensing a temperature of the refrigerant gas. The detector may be configured to detect the speed of sound through refrigerant gas in the vapor space; compare the detected speed of sound with a reference speed of sound for an uncontaminated refrigerant gas to be used for the HVACR system; and determine that a contaminant is present in the refrigerant gas of the vapor space if the detected speed of sound is different from the reference speed of sound. The detector may determine that the detected speed of sound is different from the reference speed of sound if a difference between the measured speed of sound and the reference speed of sound is greater than a predetermined threshold. The detector may be configured to detect the two-way travel time of sound in the refrigerant gas of the vapor space using an ultrasonic interferometer. The detector may be configured to calculate the molecular weight of the refrigerant gas using the measured speed of sound through the refrigerant gas, and determine the amount ratio of a contaminant in the refrigerant gas using the calculated molecular weight.

In some embodiments, the detector may include a conductive material that reacts with the contaminant and thereby has a change in the impedance thereof while the conductive material does not react to the uncontaminated refrigerant gas to be used for the HVACR system. In some embodiments, the property of the refrigerant may be an impedance of the conductive material when the refrigerant gas of the vapor space contacts the conductive material. The detector may be configured to apply a constant current to the conductive material. The metal may have a shape of a strip or wire.

In some embodiments, the property of the refrigerant gas is a thermal conductivity of the refrigerant gas. The detector may include a circuit such as, for example, a Wheatstone bridge circuit including a plurality of electrically heated filaments. In some embodiments, the detector may include a sample cell through which the refrigerant gas from the vapor space passes and a reference cell through which an uncontaminated refrigerant gas to be used for the HVACR system. The detector may detect a thermal conductivity of the refrigerant gas from the vapor space in the same cell and a reference thermal conductivity of the uncontaminated refrigerant gas in the reference cell, compare the detected thermal conductivity of the refrigerant gas in the same cell with the reference thermal conductivity, and determine that a contaminant is present in the refrigerant of the vapor space if the detected thermal conductivity of the refrigerant gas in the same cell is different from the reference thermal conductivity.

In some embodiments, the detector may include a circuit such as, for example, a Wheatstone bridge circuit, that includes a plurality of electrically heated filaments disposed in a temperature-controlled cell. In some embodiments, the circuit may detect a resistance of a first group of electrically heated filaments when the refrigerant gas from the vapor space passes the first group of the electrically heated filaments and a reference resistance of a second group of electrically heated filaments when an uncontaminated refrigerant gas to be used for the HVACR system, compare the detected resistance of the first group of the electrically heated filaments with the reference resistance, and generate a measurable voltage change if the detected resistance of the first group of the electrically heated filaments is different from the reference resistance. In response to detecting the measurable voltage change, the detector may determine that a contaminant is present in the refrigerant gas from the vapor space. In some embodiments, the Wheatstone bridge circuit includes a sample section and a reference section, and the first group of electrically heated filaments may be disposed in a sample section and the second group of electrically heated filaments may be disposed in a reference section.

In some embodiments, there is provided a method for detecting contamination of refrigerant in an HVACR system that include: detecting a property of refrigerant gas in a vapor space of the HVACR system by a detector; comparing the detected property with a reference property for an uncontaminated refrigerant gas to be used for the HVACR system; determining that a contaminant is present in the refrigerant gas of the vapor space if the detected property is different from the reference property.

Other features and aspects of the systems, methods and control concepts will become apparent from a consideration of the following detailed description and accompanying drawings.

BRIEF DESCRIPTION OF THE DRAWINGS

Reference is now made to the drawings in which like reference numbers represent corresponding parts throughout.

FIG. 3A illustrates a flow chart showing a method of detecting contamination of refrigerant in an HVACR system, according to an embodiment. FIG. 3B illustrates a flow chart showing how to output a warning that a contaminant is present in refrigerant of an HVACR system based on the determination, according to an embodiment.

DETAILED DESCRIPTION

Figure 1A:
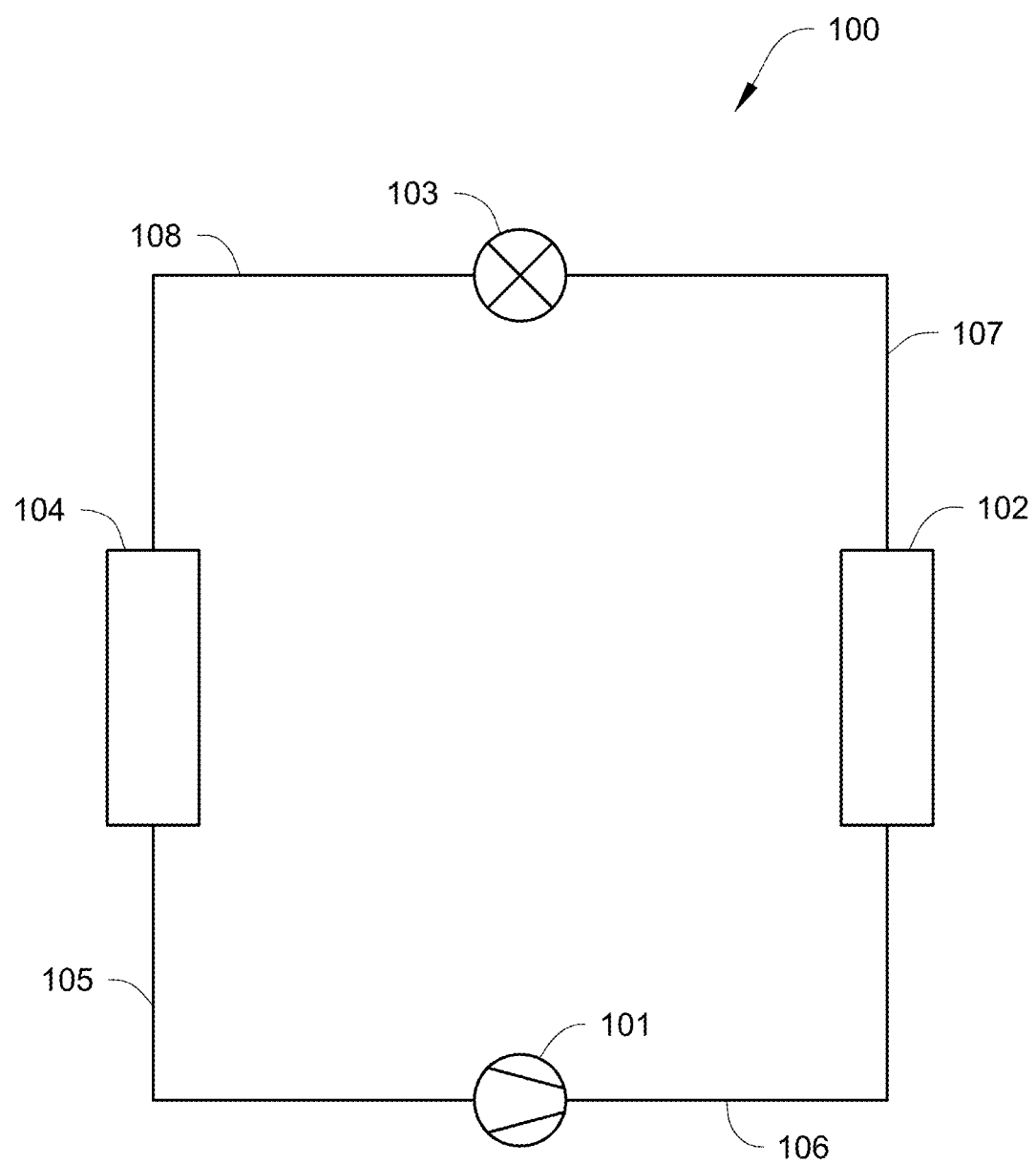
FIG. 1A illustrates a schematic diagram of an exemplary HVACR system, with which the embodiments as described herein may be accomplished.

This disclosure herein relates generally to heating, ventilation, air-conditioning and refrigeration ("HVACR") systems. More particularly, this disclosure relates to systems and methods for detecting contamination in refrigerant used in the HVACR system as well as leaks in the HVACR system.

Generally, an HVACR system uses a refrigerant to cool, heat, dehumidify or humidify a heat transfer medium such as water, air or a fluid. A refrigerant for an HVACR system includes, but are not limited to, HCFC, HFC, HCFO or HFO refrigerants or blends of these refrigerants. For example, a refrigerant for a HVACR system may include, but is not limited to, R134a and similar refrigerants with a low global warming potential ("GWP") such as R1234yf, R1234ze(E), R513A, and R516A. However, materials with similar vapor pressure and lower production cost, e.g., $CH_3Cl$ (R-40), are often used to counterfeit a refrigerant intended for the HVACR system. However, for example, the counterfeiting refrigerant R-40 is not compatible with the recent HVACR systems that generally contain aluminum and zinc and adopts a refrigerant HFC-134a (R-134a), HCFC-22 (R-22) or the like. If R-40 is used in the HVACR systems, R-40 would react with aluminum and zinc in the HVACR systems and causes system reliability issues. In addition, some of the reaction products may be severely hazardous and render the HVACR systems susceptible to damage or explosion because of high toxicity or flammability potential of the counterfeiting refrigerant. In addition, a contaminant may be introduced into the HVACR system through a leak. If the refrigerant is contaminated or counterfeited with materials other than the refrigerant to be used for the HVACR system, the HVACR system can fail to operate properly.

The existing methods of detecting refrigerant contamination in HVACR systems usually require taking a sample of the refrigerant in the HVACR system and conducting gas chromatographic work or require expensive analytical test equipment. These existing detection methods are expensive and time-consuming. The present invention provides quick, efficient, cost-saving systems or methods of determining if a contaminant or a counterfeiting refrigerant is present in an HVACR system or has been introduced into the HVACR system.

Systems for detecting contamination of refrigerant gas in an HVACR system are described herein. In some embodiments, the system may include a vapor space containing refrigerant gas; and a detector connected to the vapor space and configured to detect a property of the refrigerant gas in the vapor space, compare the detected property with a reference property for uncontaminated refrigerant gas, and determine that a contaminant is present in the refrigerant gas if the detected property is different from the reference property. In some embodiments, the system may include a controller in communication with the detector and an output device in communication with the controller. The controller may receive the determination that a contaminant is present in the refrigerant gas from the detector and generate an instruction to output the warning of the presence of contamination. In response to receiving the instruction from the controller, the output device may output a warning that indicates the presence of contamination in the refrigerant gas.

Also, methods for detecting contamination of refrigerant in an HVACR system are provided. The method may include detecting a property of refrigerant gas in a vapor space of the HVACR system by a detector; comparing the detected property with a reference property for the refrigerant gas; and determining that a contaminant is present in the refrigerant gas in the vapor space of the HVACR system if the detected property is different from the reference property. The vapor space may be a refrigerant reservoir or volume inside a component in a heat transfer circuit of the HVACR system, a fluid line in a heat transfer circuit of the HVACR system, or a refrigerant container.

HVACR System

FIG. 1A illustrates a schematic diagram of an exemplary heat transfer circuit 100 included in an HVACR system, according to some embodiments. The heat transfer circuit 100 may be applied in a variety of heating, ventilation, air-conditioning and refrigeration (HVACR) systems used to control an environmental condition (e.g., temperature, humidity, air quality, or the like) in a space (generally referred to as a conditioned space). The heat transfer circuit 100 may be specifically configured to be a cooling system (e.g., an air conditioning system) capable of operating in a cooling mode. Alternatively, the heat transfer circuit 100 may be specifically configured to be a heat pump system which may operate in both a cooling mode and a heating/defrost mode.

The heat transfer circuit 100 generally includes a compressor 101, a condenser 102, an expansion device 103, an evaporator 104 and a plurality of fluid lines 105, 106, 107, 108. The components of the heat transfer circuit 100 are fluidly connected. The heat transfer circuit 100 is exemplary and may be modified to include additional components. In some embodiments, the heat transfer circuit 100 may also include a refrigerant reservoir such as a receiver tank, an accumulator, etc., an economizer heat exchanger, one or more flow control devices, a dryer, a suction-liquid heat exchanger or the like.

The heat transfer circuit 100 operates according to generally known principles. The heat transfer circuit 100 may be configured to heat or cool heat transfer fluid or medium (e.g., a liquid such as, but not limited to, water or the like), in which case the heat transfer circuit 100 may be generally representative of a liquid chiller system. The heat transfer circuit 100 may alternatively be configured to heat or cool a heat transfer medium or fluid (e.g., a gas such as, but not limited to, air or the like), in which case the heat transfer circuit 100 may be generally representative of an air conditioner or heat pump.

In operation, a refrigerant in a gas state flows to a compressor 101. The compressor 101 compresses the refrigerant gas from a relatively lower pressure gas to a relatively higher-pressure gas. The relatively higher pressure and higher temperature gas is discharged from the compressor 101 and flows through the condenser 102. In accordance with generally known principles, the refrigerant flows through the condenser 102 and rejects heat to a heat transfer medium (e.g., water, air, etc.), thereby cooling the refrigerant. The cooled refrigerant, which is now in a liquid state, flows to the expansion device 103. The expansion device 103 reduces the pressure of the refrigerant. As a result, a portion of the refrigerant is converted to a gaseous form. The refrigerant, which is now in a mixed liquid and gaseous form flows to the evaporator 104. The refrigerant flows through the evaporator 104 and absorbs heat from a heat transfer medium (e.g., water, air, etc.), heating the refrigerant, and converting it to a gas state. The gaseous refrigerant then returns to the compressor 101. Thus, the refrigerant may flow in a gas state through a fluid line 105, flow in a liquid state through a fluid line 106, flow in a liquid state through a fluid line 107, and flow in a combination of liquid and gas states through a fluid line 108. The above-described process continues while the heat transfer circuit 100 is operating, for example, in a cooling mode (e.g., while the compressor 101 is enabled).

Figure 1B:
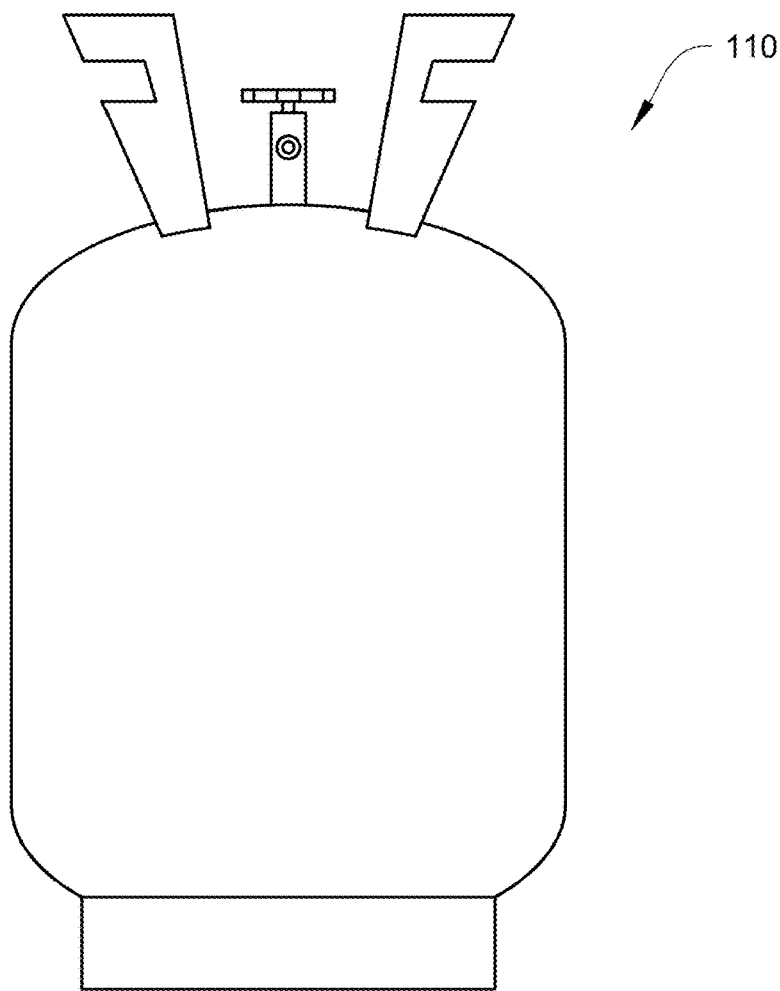
FIG. 1B illustrates a front view of an exemplary refrigerant container that may be used in an HVACR system, according to an embodiment.

In some embodiments, the HVACR system may include a refrigerant container for storing refrigerant gas or supplying refrigerant gas to the heat transfer ciruit 100. FIG. 1B illustrates an exemplary refrigerant container 110 in the HVACR system, according to some embodiments.

Contaminant Detection System

Figure 2:
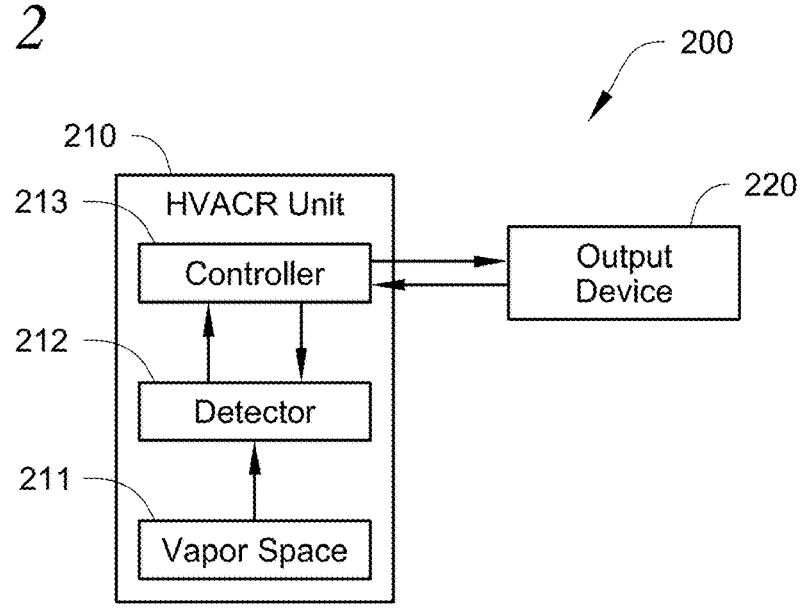
FIG. 2 illustrates a schematic block diagram of an exemplary HVACR system, according to an embodiment.

FIG. 2 illustrates a system 200 for detecting contamination of refrigerant gas in an HVACR system 210 and an output device 220 in communication with an HVACR system 210, according to some embodiments. The system for detecting contaminant of refrigerant gas may include a vapor space 211 containing refrigerant gas and a detector 212. The vapor space 211 may be a refrigerant reservoir or a fluid line in the heat transfer circuit 100, or a refrigerant container in communication with the heat transfer circuit 100. The detector 212 may be a colorimetric detector, a sound speed detector, an electric detector, a thermal conductivity detector, or the like. The system 200 may further include a controller and an output device 220 in order to inform a user of the presence of contaminant in the refrigerant gas. The detector 212 may be connected to the vapor space 211. The detector 212 may be in communication with the controller 213.

The system 200 of FIG. 2 can also be used for detecting contamination of refrigerant liquid in components of the HVACR system 210 that contains refrigerant in liquid state or are passed by the refrigerant liquid. When the system 200 detects contamination of refrigerant liquid, the system 200 includes a liquid space containing refrigerant liquid or passed by the refrigerant liquid, instead of the vapor space 211, in the HVACR system 210.

FIG. 3A illustrates a flow chart showing a method of detecting contamination of refrigerant in an HVACR system 210, according to some embodiments. If the detection of the HVACR system is initiated (step 310), the detector 212 detects a property of refrigerant gas in the vapor space 211 of the HVACR system 210 (step 312). In step 314, the detector 212 compares the detected property with a reference property for uncontaminated refrigerant gas (step 314). If the detected property is different from the reference property (step 316), the detector 212 determines that a contaminant is present in the refrigerant gas in the vapor space of the HVACR system (step 318). The detector 212 may recognize that the detected property is different from the reference property when a difference between the detected property and the reference property is greater than a predetermined threshold (step 316). Alternatively, the controller 213 may perform the steps 314, 316, 318 instead of the detector 212.

FIG. 3B illustrates a flow chart showing how to output a warning that a contaminant is present in refrigerant gas in the vapor space 212, according to some embodiments. In response to receiving the determination that a contaminant is present in the refrigerant gas in step 318, the controller 213 generates an instruction to output a warning that a contaminant is present in the refrigerant gas (step 320) and send it to the output device 220. In response to receiving the instruction from the controller 213, the output device 220 may output a warning that a contaminant is present in the refrigerant gas of the vapor space 211 (step 322).

Colorimetric Detection

In some embodiments, a property of refrigerant gas used in detecting contamination of refrigerant in the HVACR system may be a color of the reagent when the reagent is combined with the refrigerant gas in the HVACR system. In such embodiments, a system for detecting contamination of refrigerant may include a vapor space and a color detector. The color detector may include a reagent, e.g., a reactive chemical material, that would react to contaminants in the refrigerant or counterfeit refrigerants and changes a color thereof (e.g., hue and/or value of color) or results in a loss of color thereof. However, an uncontaminated refrigerant does not react with the reagent, and there would be no change of the color of the reagent. Thus, the color detector may detect the presence of contamination in the refrigerant gas if the detected color of the reagent is different from a reference color of the reagent for the refrigerant gas. The color detector may recognize that there is an effective color change in the reagent, if a difference between a level of hue and/or value of color of the reagent detected in the current refrigerant gas of the vapor space and a reference level of hue and/or value of color of the reagent in uncontaminated refrigerant gas to be used the HVACR system, is greater than a predetermined threshold. The system for detecting contamination of refrigerant may further include a controller and an output device to deliver a warning that a contaminant is present in the refrigerant gas of the HVACR system. In response to receiving the determination that a contaminant is present in the refrigerant gas, the controller generates an instruction to output a warning that a contaminant is present in the refrigerant gas and sends it to the output device. In response to receiving the instruction from the controller, the output device may output a warning that a contaminant is present in the refrigerant gas of the vapor space. The vapor space in the HVACR system may be a refrigerant reservoir or a fluid line in a heat transfer circuit, or a refrigerant container in communication with the heat transfer circuit for supplying refrigerant gas to the heat transfer circuit.

Figure 4A:
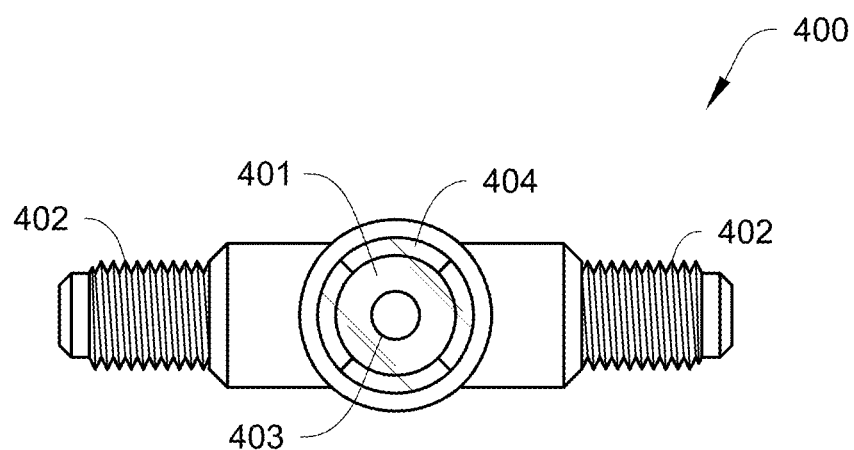
FIG. 4A illustrates a front view of a color detector for detecting contamination of refrigerant in an HVACR system, according to an embodiment.
Figure 4B:
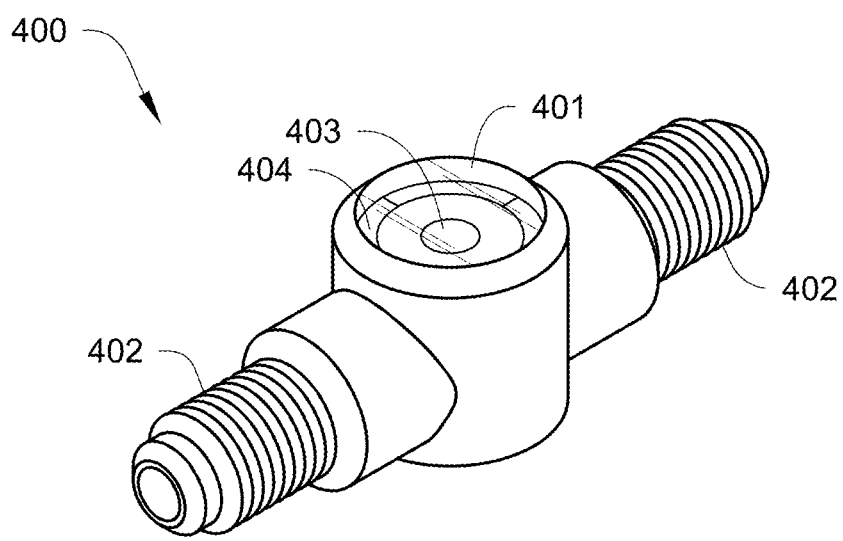
FIG. 4B illustrates a perspective view of the color detector of FIG. 4A.

FIGS. 4A and 4B illustrate a front view and a perspective view of an exemplary color detector 400 for colorimetric detection of refrigerant contamination, respectively, according to some embodiments. In FIG. 4A, the color detector 400 comprises a sight glass 401 and cylindrical refrigerant tubes 402 connecting to the sight glass 401. The sight glass 401 may include a color detecting portion 403 and a color indicator 404. The color detecting portion 403 includes a reagent and shows a color change of the reagent when there is a contaminant in the refrigerant gas from the HVACR system. The color indicator 404 may show reference levels of hue and/or value of colors indicating the type and/or amount ratio of the contaminant in the refrigerant gas. This color change of the reagent may be observed through a sight glass 401 to determine the presence of contaminants in the refrigerant gas in the HVACR system.

The color detector 400 may further comprise an internal sensor. The internal sensor may assess levels of hue and/or value of the detected color of the reagent when the refrigerant gas in the vapor space passes the reagent. The internal sensor may further compare the levels of hue and/or value of color of the reagent with the levels of hue and/or value of the reference color of the reagent in uncontaminated refrigerant gas to be used in the HVACR system, and determine that a contaminant is present in the refrigerant gas if a difference between the level and the reference level is greater than a predetermined threshold. Through the cylindrical refrigerant tubes 402, the color detector 400 may be applied in a vapor space of the HVACR system. Applying the color detector 400 in a vapor space of HVACR systems can ensure that a small amount of refrigerant would be used in the reaction for the detection, which minimizes adverse effect on the refrigerant in the HVACR system.

Figure 4C:
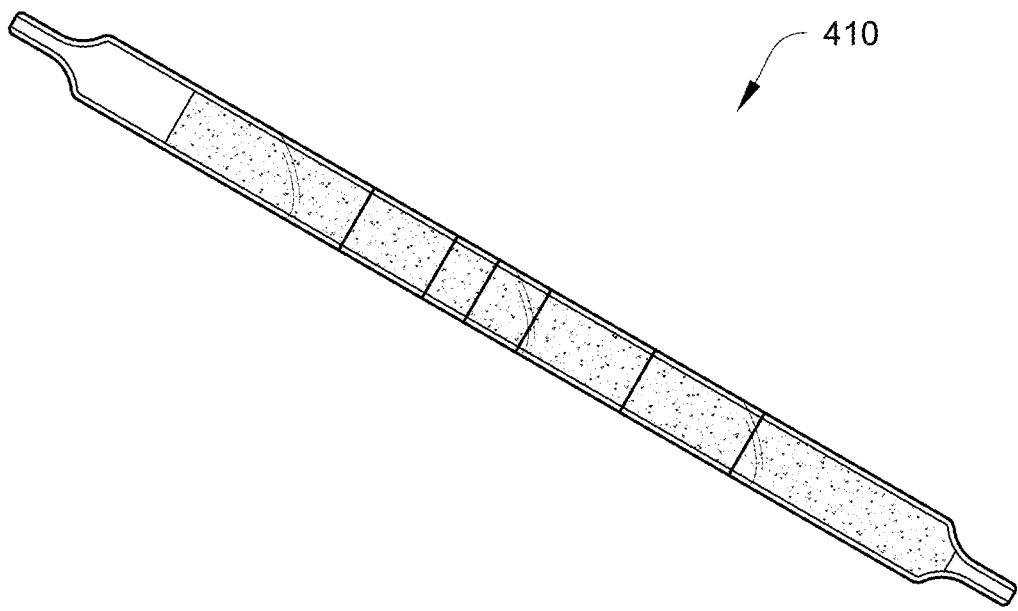
FIG. 4C illustrates another exemplary color detector for detecting contamination of refrigerant in an HVACR system, according to an embodiment.

For this colorimetric detection, numerous chemical reactions may be used to indicate the presence of certain chemicals or a certain class of chemicals in the refrigerant of an HVACR system. For example, for a contaminant such as R-40 ($CH_3Cl$) which is frequently used as a counterfeiting refrigerant, sodium chromate ($Na_2CrO_4$), sodium permanganate ($Na_2CrO_4$), etc., may be used as a reagent. Sodium chromate ($Na_2CrO_4$) is yellow in color, but would change into a white/gray color while reacting with R-40. Sodium permanganate ($Na_2CrO_4$) is originally purple in color. However, it would change to colorless when it reacts with R-40. Further, a contaminant such as R-40 containing chlorine may be exposed to sodium chromate solid for the detection. This exposure would result in a formation of chlorine ($Cl_2$) gas that reacts to some materials, which would change its color. FIG. 4C illustrates a Draeger tube detector 410 as another exemplary color detector for an HVACR system, according to some embodiments. The Draeger tube detector 410 may show a color change with the presence of potential contaminants. Various other types of color detectors may be used to perform colorimetric detection of contamination in the refrigerant gas in HVACR systems.

In operation, the color detector 400 can be configured to detect a color of the reagent in the color detecting portion 403 when the refrigerant gas from the vapor space of the HVACR system passes the reagent in the color detector 400. If there is a contaminant in the refrigerant gas or a counterfeiting refrigerant gas in the HVACR system, the reagent would react with the contaminant or counterfeiting refrigerant, and thereby have a change of color thereof. If there is no contaminant in the refrigerant gas, it will not change its color. The color detector 400 can be configured to allow a person to monitor the color change of the refrigerant gas through the sight glass 401. The person can observe the color change of the reagent through the sight glass 401 and compare the detected color of the reagent with the reference color indicated by the color indicator 404 to determine the presence of contaminants in the refrigerant gas in the HVACR system.

Alternatively, when the color detector 400 detect a color of the reagent in the color detecting portion 403, it can be configured to measure a level of hue and/or value of the color of the reagent by the internal sensor. Further, the color detector 400 can be configured to compare the measured level with a reference level of hue and/or value of color of the reagent in uncontaminated refrigerant gas to be used in the HVACR system. The color detector 400 can be configured to determine that a contaminant is present in the refrigerant gas if a difference between the measured level and the reference level is greater than a predetermined threshold.

The color detector 400 may also be used for detecting contamination of refrigerant liquid in components of an HVACR system that contains refrigerant in liquid state or are passed by the refrigerant liquid. When the color detector 400 detects contamination of refrigerant liquid, the color detector 400 is applied in a liquid space of the HVACR system containing refrigerant in liquid state, through the cylindrical refrigerant tubes 402 of the color detector 400.

The color detector 400 may be applied to an HVACR system controlling system. When a change of the reagent color is detected by the color detector 400, a controller 213 in communication with the color detector 400 may generate an instruction to output an alarm or warning and send it to an output device 220 in communication with the controller 213 in FIG. 2. In response to the instructions, the output device 220 such as, but not limited to, a display or a speaker, may output a warning indicating the presence of a contaminant in the refrigerant gas used in the HVACR system. When the warning is outputed by the output device 220, the service personnel for the HVACR system would be directed to sample the refrigerant gas in the HVACR system or conduct some further procedures to determine what the source of the reagent color change in the refrigerant gas used in the HVACR system is. Also, a portable device may be made with a controller integrated with the color detector 400 as described so that a contamination detecting system could be applied to a remote unit, refrigerant cylinder or refrigerant reclaiming device by an operator to check the presence of contaminants.

Speed of Sound Detection

In some embodiments, the property of refrigerant gas used in detecting contamination of refrigerant in an HVACR system may be a speed of sound in the refrigerant gas in the HVACR system. Contamination in the refrigerant gas may be detected by using a difference in the speed of sound between an uncontaminated refrigerant gas to be used for the HVAC unit and a contaminated refrigerant gas. In such embodiments, a system for detecting contamination of refrigerant may include a vapor space and a sound speed detector. The vapor space in the HVACR system may be a refrigerant reservoir or volume inside a component of the HVACR system, a fluid line in a heat transfer circuit of the HVACR system, or a refrigerant container in communication with the heat transfer circuit for supplying refrigerant gas to the heat transfer circuit.

The sound speed detector may detect a speed of sound in the refrigerant gas of the vapor space in an HVACR system. The speed of sound is a distance traveled per unit time by a sound wave propagating through a medium (i.e., the refrigerant gas). The speed of sound in an ideal gas may be given by the relationship below:

$$v = \sqrt{\frac{\gamma RT}{M}},$$

wherein v is the speed of sound through refrigerant gas, γ is an adiabatic constant (characteristic of a specific gas), R is a universal gas constant (8.314 J/mol K), M is a molecular weight of refrigerant gas (kg/mol), and T is an absolute temperature. From the above equation, the speed of sound may be used to detect small changes in molecular weight of gas.

The sound speed detector may compare the detected speed of sound in the refrigerant gas of the vapor space in the HVACR system with a reference speed of sound for uncontaminated refrigerant gas to be used for the HVACR system. Table 1 shows reference speeds of sound in various refrigerants in gas state.

TABLE 1

Speed of sound for various refrigerants in gas state

| Refrigerant | Speed of Sound (m/s) at 273° K and 1 atm |
|---|---|
| Oxygen* | 315 |
| Nitrogen* | 337 |
| R-22 (chlorodifluoromethane)* | 174 |
| R-32 (difluoromethane)* | 231 |
| R-134a (1,1,1,2-tetrafluoroethane)* | 154 |
| R-1234yf (2,3,3,3-tetrafluoropropene)* | 144 |
| R-410A (mixture of difluoromethane and pentafluoroethane)*s | 189 |
| R-290 (propane)* | 238 |
| R-40 (methyl chloride)** | 235 |

*REFPROP v9
**REFPROP v9 by international approximation via Brown/Joback methods If the detected speed of sound is different from the reference speed of sound for the refrigerant gas, the sound speed detector may determine that a contaminant is present in the refrigerant gas in the vapor space of the HVACR system. The sound speed detector may recognize that the detected speed of sound is different from the reference speed of sound when a difference between the detected speed of sound and the reference speed of sound is greater than a predetermined threshold. The system for detecting contamination of refrigerant may further include a controller and an output device to deliver a warning that a contaminant is present in the refrigerant gas. In response to receiving the determination that a contaminant is present in the refrigerant gas, the controller generates an instruction to output a warning that a contaminant is present in the refrigerant gas and send it to the output device. In response to receiving the instruction from the controller, the output device may output a warning that a contaminant is present in the refrigerant gas of the vapor space.

Further, the sound speed detector may calculate a molecular weight of the refrigerant gas using the detected speed of sound through the refrigerant gas. If the average molecular weight of the refrigerant gas in the vapor of the HVACR system is different from a reference molecular weight of an uncontaminated refrigerant gas to be used in the HVACR system, it would be an indication of the wrong refrigerant, contaminated refrigerant, or a change in the blend composition. The sound speed detector may also determine the amount ratio of the contaminant in the refrigerant gas using the calculated molecular weight of the current refrigerant gas and the reference molecular weight of the uncontaminated refrigerant gas to be used in the HVACR system.

Figure 5:
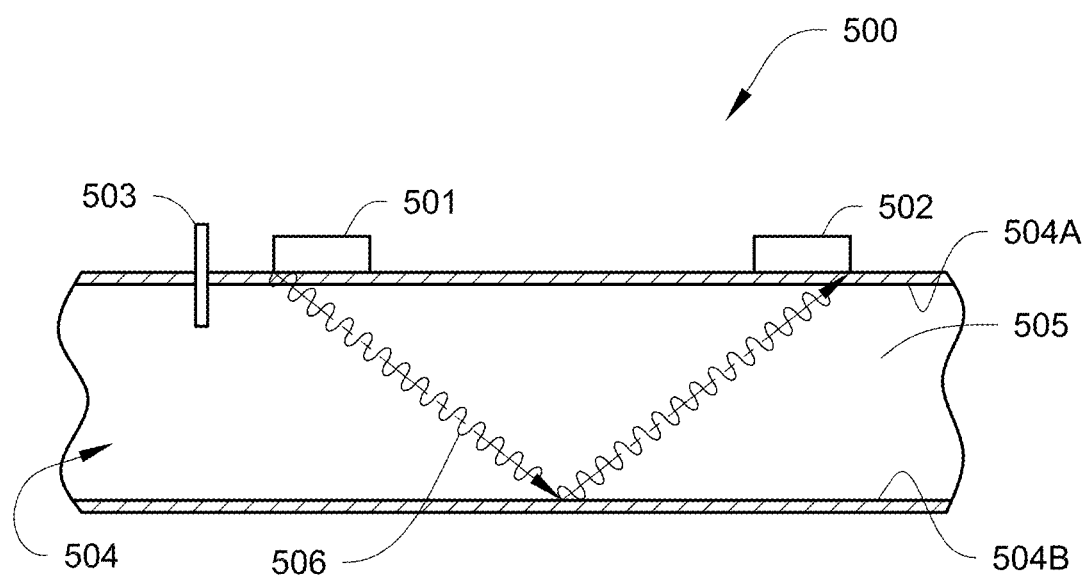
FIG. 5 illustrates a schematic diagram of an exemplary speed of sound detector for detecting contamination of refrigerant gas in an HVACR system, according to an embodiment.

FIG. 5 illustrates a schematic diagram of an exemplary speed of sound detecting system to detect contamination of refrigerant gas in an HVACR system, according to some embodiments. In one embodiment, the speed of sound detecting system may use an ultrasonic interferometer as a sound speed detector to detect the speed of sound in the refrigerant gas. Other detectors may be used to detect the contaminant in the refrigerant of the HVACR system. The ultrasonic interferometer measures a two-way travel time of sound through a vapor space that there is refrigerant gas. In one embodiment, the vapor space may be a fluid line of gas state in the HVACR system. The vapor space may be also a refrigerant reservoir in the HVACR system, a refrigerant container in communication with the HVACR system, or the like.

As illustrated in FIG. 5, a sound speed detector 500 may include a transducer 501 outputting acoustic signals, e.g., sound waves 506, into the vapor space (e.g., fluid line) 504 for the refrigerant gas 505 and a receiver 502 receiving the sound waves 506 transmitted or reflected. The detector 500 may also include a sensor 503 for sensing a temperature in the vapor space of the HVACR system. When the sound waves 506 from the transducer 501 propagate through the refrigerant gas 505 in the vapor space 504 of an HVACR system, the sound waves 506 encounter a wall of the vapor space 504. Then, a part of the energy of the sound wave 506 is transmitted through the vapor space 504/refrigerant gas 505 interface while the other part of the energy of the sound wave is reflected back to the receiver 502. The degree to which the energy of the sound wave 506 is split between the transmitted wave and the reflected wave is a function of impedance (Z) difference between the wall of the vapor space 504 and the refrigerant gas 505. The impedance (Z) may be given by a product of a speed of sound and a density of each material. In this case, the reflected waves in the fluid line may be in phase or out of phase by ½ wavelength, depending on how high the impedances of material for the pipe or the refrigerant gas are or which one of the impedance of the pipe material and the impedance of the refrigerant gas is higher.

In operation, the sound speed detector 500 can be configured to detect the speed of sound through a refrigerant gas 505 in the vapor space of the HVACR system. There are many ways of detecting the speed of sound through the refrigerant gas. For example, the sound speed detector 500 may measure a two-way travel time of sound through, for example, a refrigerant gas fluid line (e.g., 504) that contains the refrigerant gas 505 to detect the speed of sound. The sound speed detector 500 can be configured to compare the detected speed of sound with a reference speed of sound for an uncontaminated refrigerant gas. The sound speed detector 500 can be configured to determine that a contaminant is present in the refrigerant gas if the detected speed of sound is different from the reference speed of sound. The sound speed detector 500 may recognize that the detected speed of sound is different from the reference speed of sound when a difference between the detected speed of sound and the reference speed of sound is greater than a predetermined threshold. The sound speed detector 500 can be also configured to calculate a molecular weight of the refrigerant gas using the detected speed of sound through the refrigerant gas. The sound speed detector 500 can be configured to determine that there is a wrong refrigerant, a contaminated refrigerant, or a change in the blend composition in the refrigerant gas of the vapor space if the average molecular weight of the refrigerant gas in the vapor of the HVACR system is different from a reference molecular weight of an uncontaminated refrigerant gas to be used in the HVACR system. The sound speed detector may also determine the amount ratio of the contaminant in the refrigerant gas using the calculate molecular weight of the refrigerant gas in the vapor space and the reference molecular weight of the uncontaminated refrigerant gas to be used in the HVACR system.

In some embodiments, there may be internal echoes in a vapor space of the HVACR system. In that case, a first sound wave returning from a back surface 504B of the vapor space 504 will also produce a sound wave that reflects off the back surface 504B and returns to the receiver 502, as illustrated in FIG. 5. The sound wave will not be out of phase because it does not change its phase while bouncing internally at the back surface 504B. When the echoing sound waves encounter the next pulse of sound waves coming through the vapor space 504, they interact with the next pulse of sound waves, constructively or destructively. For constructive interference to occur, the number of wavelengths between the surfaces of the corresponding space in the vapor space 504 may be an integer or half-integer number. The sound wave times between sound pulses may be determined when the amplitude of the returning echoes is maximized and minimized. From this data, the two-way travel time of the sound wave may be obtained. The temperature would also need to be known to compare it to reference data about the speed of sound for a specific refrigerant. The sensor 503 may detect a temperature in the fluid line. If the sound speed detector 500 does not include the sensor 503, it may include a reference cell containing an uncontaminated refrigerant gas to be used in the HVACR system in which a reference speed of sound for the refrigerant gas can be obtained. In this case, data obtained from the refrigerant gas in the HVACR system can be compared with the reference speed of sound obtained from the reference cell to detect the difference in the speed of sound.

The sound speed detector 500 may also be used for detecting contamination of refrigerant liquid in components of an HVACR system that contains refrigerant in liquid state or are passed by the refrigerant liquid. In that case, a sound speed detector 500 may include a transducer 501 outputting acoustic signals, e.g., sound waves 506, into a liquid space (e.g., fluid line) 504 for the refrigerant liquid 505 and a receiver 502 receiving the sound waves 506 transmitted or reflected. In an embodiment, the sound waves 506 may travel through a front surface 504A of the fluid line. Various sound speed detector according to the present invention as described above may be applied to an HVACR system controlling system. When a change of the speed of sound in refrigerant is detected by the sound speed detector, a controller 213 in communication with the sound speed detector may generate an instruction to output an alarm or warning and send it to an output device 220 in communication with the controller 213 in FIG. 2. In response to the instructions, the output device 220 such as, but not limited to, a display or a speaker, may output a warning indicating the presence of a contaminant in the refrigerant gas used in the HVACR system. When the warning is outputed by the output device 220, the service personnel for the HVACR system would be directed to sample the refrigerant gas in the HVACR system or conduct some further procedures to determine what the source of the speed change of sound in the refrigerant gas used in the HVACR system is. Also, a portable device may be made with a controller integrated with the sound speed detector as described so that a contamination detecting system could be applied to a remote unit, refrigerant cylinder or refrigerant reclaiming device by an operator to check the presence of contaminants.

Figure 6:
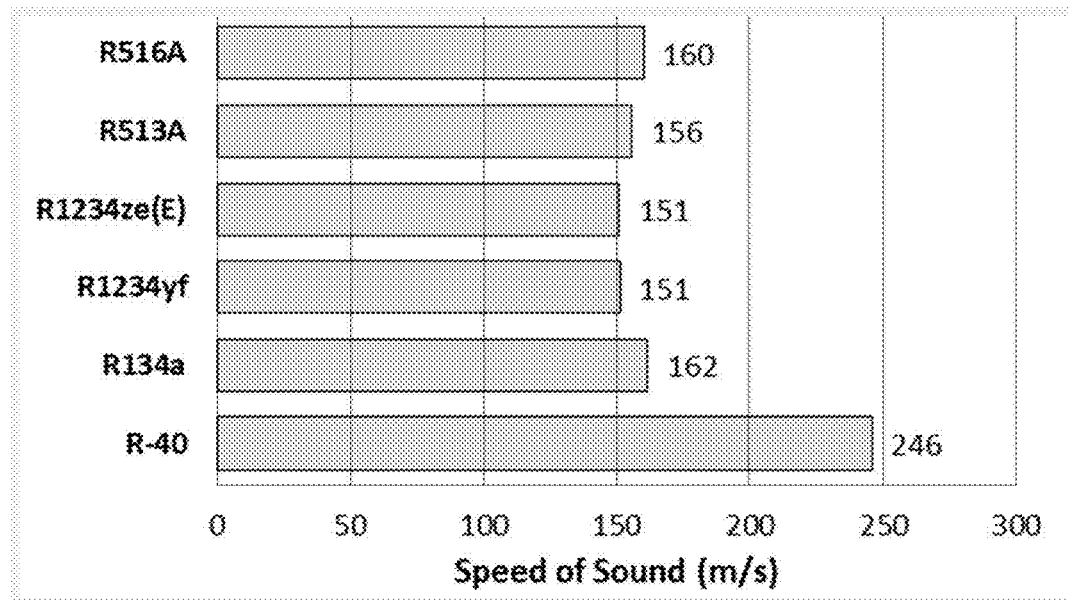
FIG. 6 illustrates a speed of sound through each of R134a, R1234yf, R1234ze(E), R513A, and R516A, and R-40.

FIG. 6 illustrates the speed of sound through each of R134a, R1234yf, R1234ze(E), R513A, and R516A, and R-40 in the gas phase as at 25° C. and 1 atm in an embodiment. One or more of R1234yf, R1234ze(E), R513A, and R516A may be used as alternatives with low global warming potential ("GWP") for R134a in some embodiments. The speed of sound of each refrigerant was obtained from REFPROP v 9.1. As discussed previously, the refrigerant in HVAC systems that utilize R-134a may be counterfeited with R-40 as R-40 has similar vapor properties and is inexpensive relative to R134a or its alternatives. However, R-40 is flammable and is toxic at low levels, such that it is classified as B2 in ASHRAE Standard 34. In an embodiment, R-40 is a contaminant in a HVACR system that is designed to utilize a refrigerant of R134a or one of its low GWP alternatives.

As shown by FIG. 6, the speed of sound through R-40 is approximately 246 m/s. The speed of sound through R134a or its low GWP alternatives is between 151 m/s and 162 m/s. Thus, R-40 has a speed of sound that is between 52% (for R134a) and 63% (for R1234ze(E) and R1234yf) greater relative to the speed of sound of R-40 than R134a and its low GWP alternatives. As such, a sound speed detector for of an HVACR system utilizing a refrigerant such as R134a and/or one of its low GWP alternatives can determine if the refrigerant contains a contaminant (e.g., R-40).

Figure 7:
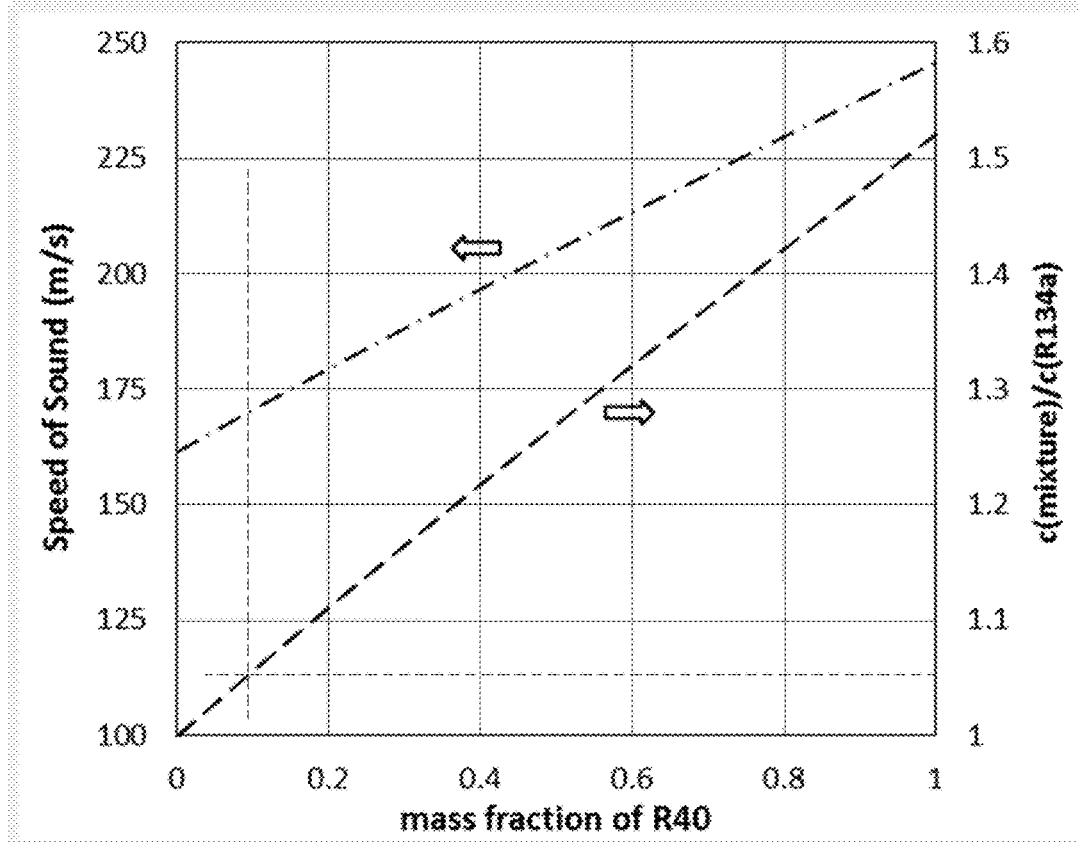
FIG. 7 illustrates a graph of a speed of sound through refrigerant mixtures of R134a and/or R-40, according to an embodiment.

FIG. 7 shows the speed of sound through various mixtures of R-40 and R134a at 25° C. and 1 atm in an embodiment. The speed of sound of the various mixtures was modeled using REFPROP v 9.1. The dashed and dotted line shows values (in m/s) of the speed of sound of a refrigerant mixture of R-40 and R134a as the mass fraction of R-40 is varied. The speed of sound of a refrigerant mixture increases as it includes more R-40.

The dashed line in FIG. 7 shows the speed of sound of a refrigerant mixture relative to the speed of sound through R134a. As shown by the dashed line, the speed of sound of the refrigerant mixture is a linear function of the mass fraction of R-40. The other low GWP alternatives of R134a were also modeled in REFPROP as refrigerant mixture with R-40. Each of the low GWP alternatives had a similar linear relationship between the mass fraction of R-40 and the speed of sound of the refrigerant mixture of the low GWP alternative and R-40.

As shown by the vertical dashed line and horizontal dashed line in FIG. 7, a detector (e.g., sound speed detector 500) that is able to detect a 5% change in the speed of sound of a refrigerant would be able to detect when the refrigerant has 10% or more of a contaminant such as R-40 in an embodiment. A detector that is able to detect a 2% change in the speed of sound of a refrigerant would be able to detect when the refrigerant has 4% of more of a contaminant such as R-40 in an embodiment. A detector that is able to detect a 10% change in the speed of sound of a refrigerant would be able to detect when the refrigerant contains 20% or more of a contaminant such as R-40 in an embodiment.

Impedance Detection

Contamination in refrigerant gas in an HVACR system may be detected by determining a difference in electrical impedances between a refrigerant gas to be used for the HVACR system and contaminants. In such embodiments, a property of refrigerant gas used in detecting contamination of refrigerant in the HVACR system may be an impedance of a conductive material when combined with the refrigerant in the vapor space of the HVACR system. A system for detecting contamination of refrigerant may include a vapor space and an electrical detector. The vapor space in the HVACR system may be a refrigerant reservoir or volume inside a component of a heat transfer circuit, a fluid line in a heat transfer circuit, or a refrigerant container in communication with the heat transfer circuit for supplying refrigerant gas to the heat transfer circuit.

The electrical detector may include a conductive material that is reactive to the potential contaminants or counterfeiting refrigerants while it does not react to an uncontaminated refrigerant gas to be used for the HVACR system. The electrical detector may detect the impedance of the conductive material when the electrical detector is applied to refrigerant gas in the vapor space of the HVACR system. The electrical detector may compare the detected impedance with a reference impedance of the conductive material in uncontaminated refrigerant gas to be used for the HVACR system, and determine that a contaminant is present in the refrigerant gas in the vapor space if the detected impedance is different from the reference impedance. The electrical detector may recognize that the detected impedance is different from the reference impedance when a difference between the detected impedance and the reference impedance for the refrigerant gas is greater than a predetermined threshold.

Figure 8:
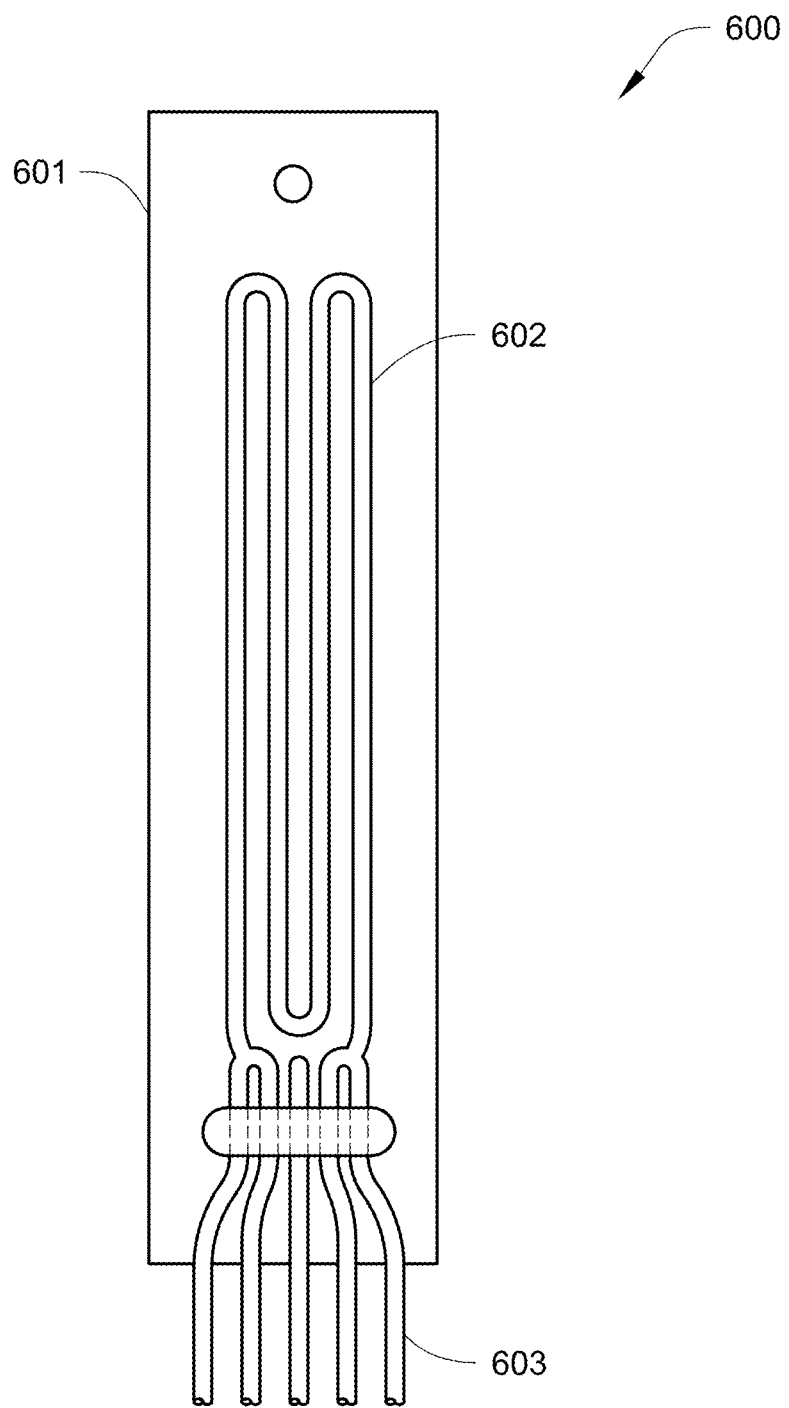
FIG. 8 illustrates a circuit board included in an exemplary electrical detector for detecting contamination of refrigerant gas in an HVACR system, according to an embodiment.

FIG. 8 illustrates a circuit board portion of an exemplary electrical detector 600 for detecting contamination of refrigerant gas in an HVACR system, according to some embodiments. The electrical detector may include a circuit board 601, a metal portion 602 and wires 603. The wires 603 are connected to the metal 602 for detecting an impedance of the metal 602 in the refrigerant gas. The metal 602 is reactive to the potential contaminants in the refrigerant gas and changes the impedance thereof. However, the metal 602 does not react to an uncontaminated refrigerant gas to be used for the HVACR system. For example, for detection of a potential contaminant R-40 in a refrigerant gas, the metal 602 may be made of a material including, but not limited to, zinc, magnesium or other materials to react with R-40. If there is R-40 in a vapor space of the HVACR system which the electrical detector is applied to, R-40 would react with the metal 602 and form iron-chlorides or organometallic compounds on the surface of the metal 602. Then, the R-40 would change an impedance of the metal 602. The metal 602 may be formed in a shape such as, but not limited to, a strip, a wire or the like.

In operation, the electrical detector can be configured to detect an impedance of the metal 602 in the refrigerant gas from the vapor space in the HVACR system. The electrical detector can be configured to compare the impedance of the metal 602 with a reference impedance for the metal 602 in an uncontaminated refrigerant gas. The electrical detector can be configured to determine that a contaminant is present in the refrigerant gas if the detected impedance of the metal is different from the reference impedance. The electrical detector may recognize that the detected impedance of the metal is different from the reference impedance, when a difference between the detected impedance and the reference impedance is greater than a predetermined threshold. In an embodiment, current is applied at times in the electrical detector 600 to detect properly the impedance change of the metal 602. In an embodiment, current can be constantly applied in the electrical detector 600. Further, the impedance of the metal 602 may be obtained by detecting a voltage and/or resistance of the metal in the refrigerant gas. The impedance of the metal 602 may be detected and monitored by the circuit board 601 connected to the metal 602. The impedance change of the metal 602 indicates that the metal 602 has reacted with reactive contaminant included in the refrigerant of the HVACR system. Thus, the electrical detector can determine that the refrigerant of the HVACR system is contaminated. Further, based on a difference between the detected impedance and the reference impedance for the metal 602, the electrical detector can determine what kind of contaminant is present in the refrigerant gas in the HVACR system and/or at what amount ratio the contaminant is present in the refrigerant gas.

For the impedance detection, the electrical detector may be in some embodiments applied to a vapor space of a non-running HVACR system. In some circumstances, the electrical detector can be effective when the HVACR system is not running, to avoid variation in cooling of the metal configuration and/or contamination by lubricant of the HVACR system.

The electrical detector 600 may also be used for detecting contamination of refrigerant liquid in components of an HVACR system that contains refrigerant in liquid state or are passed by the refrigerant liquid. In that case, the system for detecting contamination of refrigerant may include a liquid space containing refrigerant liquid and an electrical detector 600. The electrical detector may include the metal portion 602 for detecting an impedance of the metal 602 in the refrigerant liquid. The metal 602 is reactive to the potential contaminants in the refrigerant liquid and changes the impedance thereof while the metal 602 does not react to an uncontaminated refrigerant liquid to be used for the HVACR system.

Various electrical detector according to the present invention as described above may be applied to an HVACR system controlling system. When a change of electrical impedance of conductive material in refrigerant gas is detected by the electrical detector, a controller 213 in communication with the electrical detector may generate an instruction to output an alarm or warning and send it to an output device 220 in communication with the controller 213 in FIG. 2. In response to the instructions, the output device 220 such as, but not limited to, a display or a speaker, may output a warning indicating the presence of a contaminant in the refrigerant gas used in the HVACR system. When the warning is outputted by the output device 220, the service personnel for the HVACR system would be directed to sample the refrigerant gas in the HVACR system or conduct some further procedures to determine what the source of electrical impedance change of conductive material in the refrigerant gas used in the HVACR system is. Also, a portable device may be made with a controller integrated with the electrical detector according to the present invention so that a contamination detecting system could be applied to a remote unit, refrigerant cylinder or refrigerant reclaiming device by an operator to check the presence of contaminants.

Thermal Conductivity Detection

In some embodiments, the property of refrigerant used in detecting contamination of refrigerant gas in an HVACR system is a thermal conductivity of the refrigerant gas in the HVACR system. In such embodiments, a system for detecting contamination of refrigerant gas may include a vapor space and a thermal conductivity detector (TCD). The vapor space in the HVACR system may be a refrigerant volume or reservoir in a heat transfer circuit, a fluid line in a heat transfer circuit, or a refrigerant container in communication with the heat transfer circuit for supplying refrigerant gas to the heat transfer circuit. Contamination of refrigerant may be detected by detecting a difference in thermal conductivity between a refrigerant gas to be used for the HVACR system and contaminants or counterfeiting refrigerants with the TCD. The TCD may be a bulk property detector. The TCD may be a chemical specific detector used in gas-liquid chromatography, for example, a Katharometer. The TCD may detect a thermal conductivity in a refrigerant gas of the vapor space in the HVACR system. Table 2 shows thermal conductivities of various refrigerant gases.

TABLE 2

Thermal conductivity of refrigerant gas

| Refrigerant | Thermal Conductivity (mW/m · K) at 273° K and 1 atm. |
|---|---|
| Oxygen* | 24.3 |
| Nitrogen* | 24.0 |
| R-22* | 9.1 |
| R-32* | 11.0 |
| R-134a* | 11.4 |
| R-1234yf* | 11.7 |
| R-410A* | 11.5 |
| R-290 (propane)* | 15.6 |
| R-40** | 10.5 |

*REFPROP v9
**http://encyclopedia.airliquide.com/encyclopedia.asp?GasID=18

The TCD may compare the detected thermal conductivity of the refrigerant gas with a reference thermal conductivity of the uncontaminated refrigerant gas to be used for the HVACR system. If the detected thermal conductivity is different from the reference thermal conductivity, the TCD may determine that a contaminant is present in the refrigerant gas of the vapor space in the HVACR system. The TCD may recognize that the detected thermal conductivity is different from the reference thermal conductivity when a difference between the detected thermal conductivity and the reference thermal conductivity is greater than a predetermined threshold.

Figure 9A:
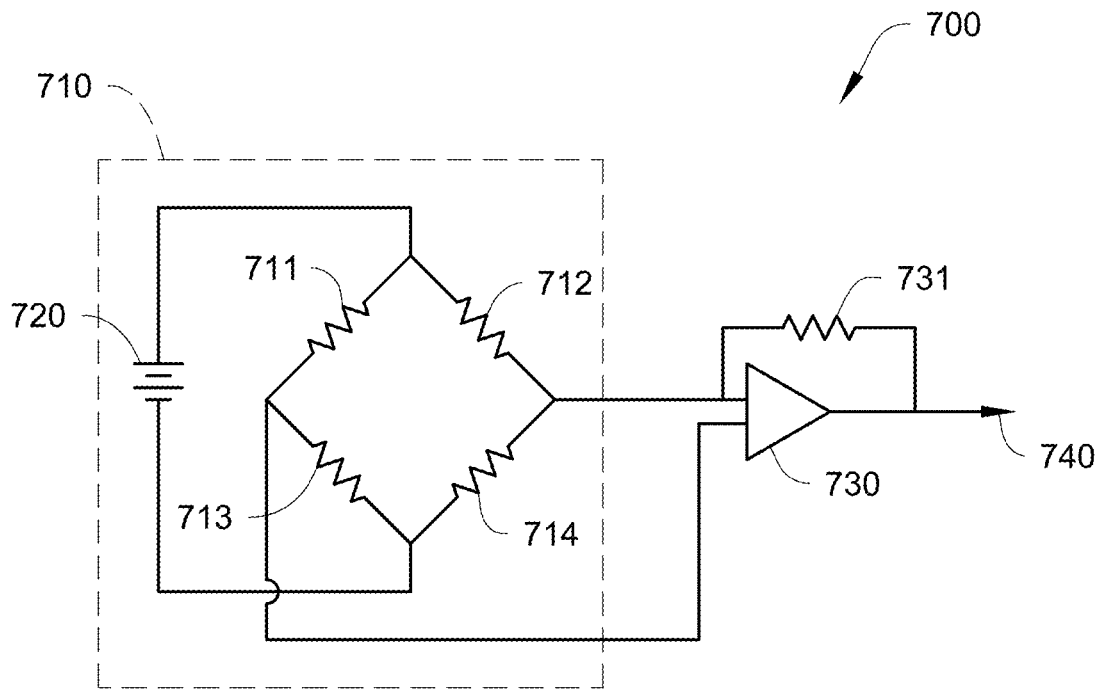
FIG. 9A illustrates a schematic diagram of an exemplary thermal conductivity detector for detecting contamination of refrigerant gas in an HVACR system, according to an embodiment.

FIG. 9A illustrates a schematic diagram of an exemplary TCD 700 for detecting contamination of refrigerant gas in an HVACR system, according to some embodiment. The TCD 700 may include a circuit 710 (e.g., a Wheatstone bridge circuit including two pairs of electrically heated filaments 711, 712, 713, 714) for sensing difference in thermal conductivity between the refrigerant gas and uncontaminated refrigerant gas to be used for the HVACR system. The TCD 700 may also include a power supply 720, an amplifier 730 (that may include a resistance 731) and/or other components (not shown). The TCD may be in communication with a record or a detector display 740.

Figure 9B:
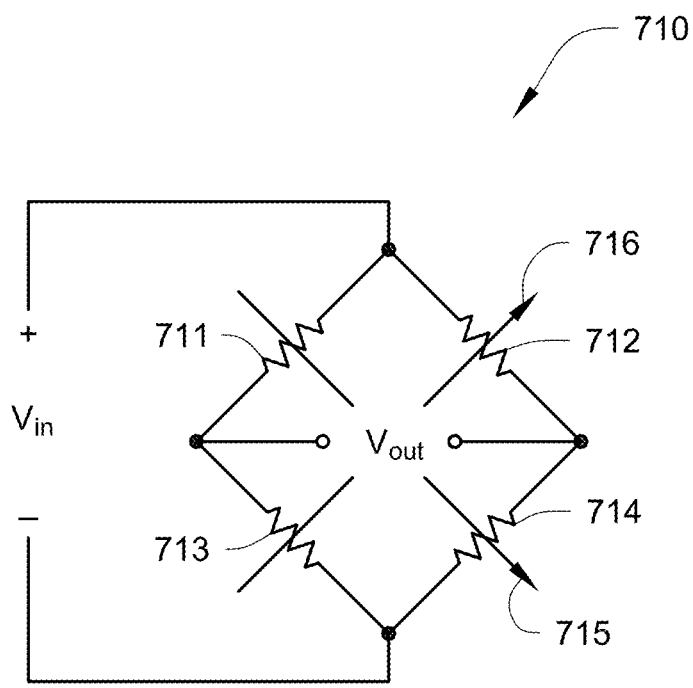
FIG. 9B illustrates a schematic diagram of a Wheatstone bridge circuit that may be included in the thermal conductivity detector.

FIG. 9B illustrates a schematic diagram of an exemplary circuit 710 for sensing the difference in thermal conductivity between the sample gas to be measured and the reference gas. When the circuit 710 is a Wheatstone bridge circuit, it uses four matched filaments 711, 712, 713, 714 that change resistance according to the thermal conductivity of the gas passing over it. A reference gas, e.g., an uncontaminated refrigerant gas to be used for an HVACR system, flows into the filaments 711 and 714. A sample gas to be measured, e.g., the actual refrigerant gas from a vapor space of the HVACR system, or a combination of the carrier gas and the sample gas may flow into the filaments 712 and 713. An arrow 715 is a flow of the reference gas and an arrow 716 is a flow of the sample gas. The reference gas flow and the sample gas flow are temperature-controlled in the circuit 710. When resistances of all four filaments 711, 712, 713, 714 are the same, Vout as shown in the middle of the Wheatstone bridge circuit 710 is zero, which means that all the fillaments are passed by the same gas as the reference gas. In this case, there is a stable heat flow from the filaments 711, 712, 713, 714 to a detector body (not shown). However, when the sample gas 716 different from the reference gas passes over half of the bridge, i.e., filaments 713, 712, Vout's value correlates to the content of the sample gas 716. When there is a difference of the thermal conductivity between the sample gas flow 716 and the reference gas flow 715, the filaments of the circuit 710 heat up and change resistance thereof. This resistance change is detected by the circuit 710. Then, the circuit 710 may produce a measurable voltage change Vout. The circuit 710 operates to detect the resistance change and produce a measurable voltage change according to generally known principles.

Figure 9C:
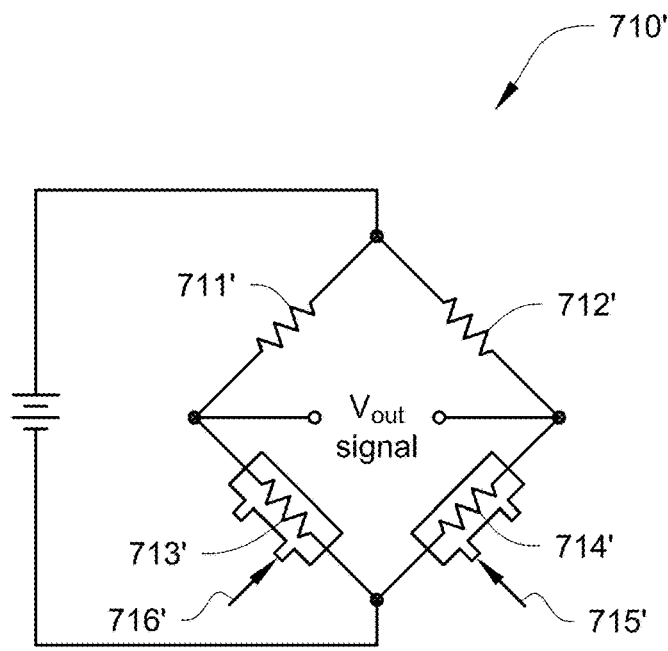
FIG. 9C illustrates a portion of a cell that may be used in the thermal conductivity detector.

FIG. 9C illustrates another exemplary Wheatstone bridge circuit 710' for sensing the difference in thermal conductivity between the sample gas and the reference gas. In FIG. 9C, the circuit 710' includes four electronically heated filaments 711', 712', 713', 714'. The circuit 710' may produce a measurable voltage change Vout signal to be detected by the TCD 700 when reference gas flow 715' passing the filament 714' and the sample gas flow 716' passing the filament 713' have different thermal conductivity.

Figure 9D:
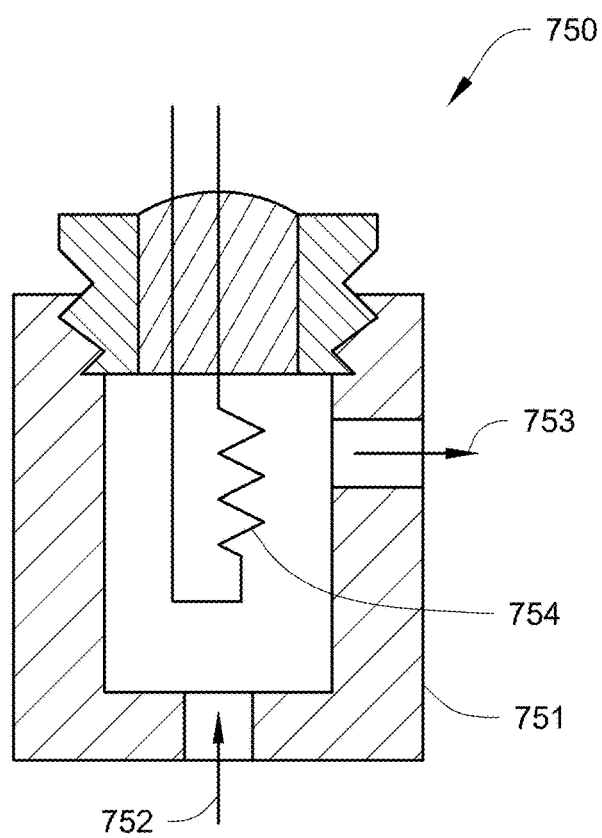
FIG. 9D illustrates a part of an exemplary cell for a filament of a thermal conductivity detector, according to an embodiment.

FIG. 9D illustrates a part of an exemplary cell 750 for each filament of the circuit 710, according to some embodiments. The part of the cell 750 may comprise an input of gas flow 752, an output of gas flow 753 and a filament 754. The filament 754 in FIG. 9D may correspond to any of filaments 711, 712, 713, 714 in FIG. 9B and 711', 712', 713', 714' in FIG. 9C.

The TCD 700 may be also responsive to non-condensable gas, for example, argon, oxygen, nitrogen or carbon dioxide. Therefore, if air or other gas enters the HVACR system during a repair and stays in the HVACR system after the repair, the TCD 700 may detect the air or other gas. In an embodiment, Katharometer may be used as the TCD. Katharometer is inexpensive and has good accuracy, such as, but not limited to, when the gas in question are known.

In operation, the TCD 700 can be configured to detect a thermal conductivity of refrigerant gas in the sample cell, which flows from the vapor space of the HVACR system and a thermal conductivity refrigerant in the reference cell. The TCD 700 can be configured to compare the thermal conductivity of refrigerant gas flow 716 in the sample cell with a reference thermal conductivity of refrigerant gas flow 715 in the reference cell. The TCD can be configured to determine that a contaminant is present in the refrigerant gas flow 716 in the sample cell if the thermal conductivity of refrigerant gas flow 716 is different from the reference conductivity of refrigerant gas flow 715. The TCD 700 may recognize that the thermal conductivity of refrigerant gas flow 716 is different from the reference thermal conductivity of refrigerant gas flow 715 when a difference between the thermal conductivity of refrigerant gas flow 716 and the reference thermal conductivity of refrigerant gas flow 715 is greater than a predetermined threshold.

In another embodiment, the circuit 710 in the TCD 700 can be configured to detect a resistance change in electrically heated filaments 712, 713 when the refrigerant gas 716 from the vapor space of the HVACR system passes the filaments 712, 713. The circuit 710 can be also configured to detect a reference resistance change in the electrically heated filaments 711, 714 when the uncontaminated refrigerant gas 715 to be used for the HVACR system passes the filaments 711, 714. The circuit 710 can be configured to compare the resistance of the filaments 712, 713 with the reference resistance of the filaments 711, 714. The circuit 710 can be configured to generate a measurable voltage change when the resistance of the filaments 712, 713 is different from the resistance of the filaments 711, 714. The TCD 700 can be configured to determine that a contaminant is present in the refrigerant gas from the vapor space of the HVACR system when the TCD 700 detects the measurable voltage change generated by the circuit 710.

Figure 10:
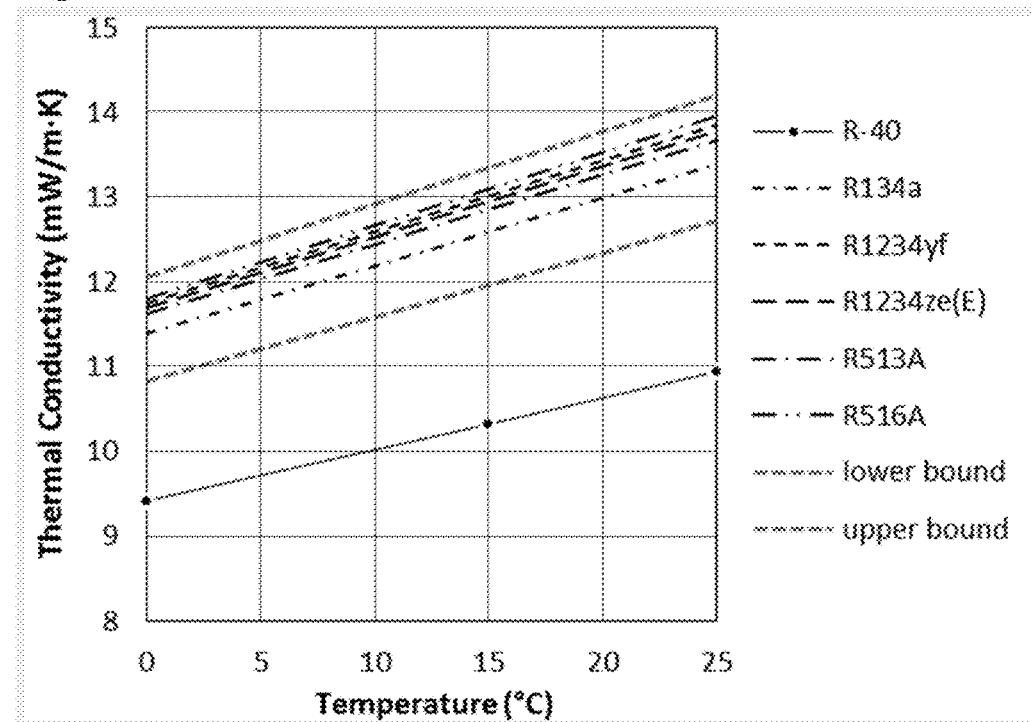
FIG. 10 illustrates the thermal conductivities of each of R134a, R1234yf, R1234ze(E), R513A, and R516A, and R-40.

FIG. 10 illustrates the thermal conductivities of R134a, R1234yf, R1234ze(E), R513A, and R516A, and R-40 in the gas phase as a function of temperature at pressure of 1 atm in an embodiment. The thermal conductivities of R134a, R1234yf, R124ze(E), were modeled using REFPROP a based on experimental measurements. R-513A is a blend of R-1234yf and R-134A. R-516A is a mixture of mainly R1234yf with R134a and R152a. The thermal conductivity of R152a is slightly higher than R123a and R1234yf. The thermal conductivity for R513A and R-516A were modeled using empirical mixing rules and REFPROP. The thermal conductivity of R-40 is based on the thermodynamic properties of methyl chloride. As discussed previously, the refrigerant in HVAC systems that utilize R-134a or one of its low GWP alternatives may be counterfeited with R-40.

The measured thermal conductivity for R134a has an uncertainty of 5%. The measured thermal conductivities for R-1234yf and R-1234ze(E) have an uncertainty of 3%. Thus, an upper bound for R-134a and its low GWP alternatives is based on R-1234ze(E) plus its 3% experimental uncertainty. The upper bound is shown in FIG. 10 by the dashed line above R516A. A lower bound for R-134a and its low GWP alternatives is based on R-134a minus its 5% experimental uncertainty. The lower bound is shown in FIG. 10 by the dashed line below R-134a.

As shown by FIG. 10, there is a significant difference in the thermal conductivity of R-40 relative to R134a and its low GWP alternatives. For example, there would be approximately a 15% difference relative to the thermal conductivity of R-40 in the thermal conductivity between the lower bound and R-40 at 0° C. Thus, a detector (e.g., TCD 700) for a HVACR system can be used to detect if a refrigerant (e.g., R134a, R1234yf, R1234ze(E), R513A, and/or R516A) contains a contaminant (e.g., R-40) based on the thermal conductivity of the refrigerant in an embodiment.

Figure 11:
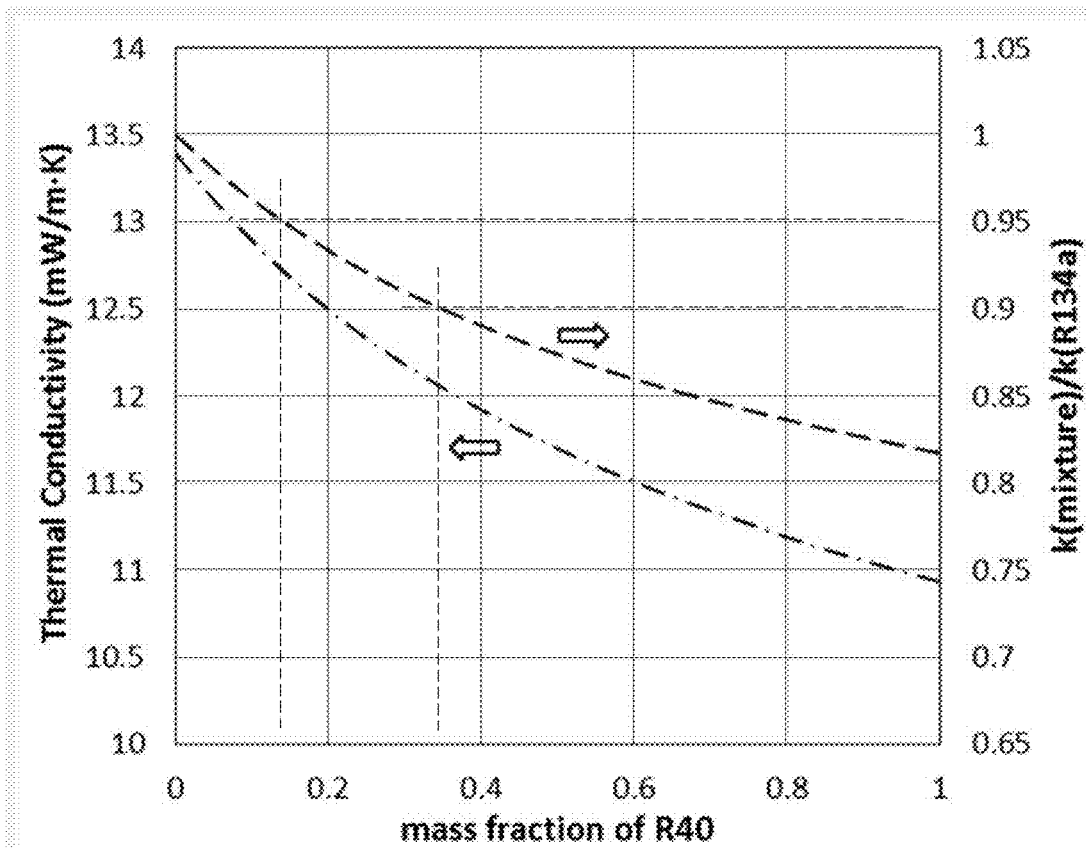
FIG. 11 illustrates the thermal conductivities of refrigerant mixtures of R134a and/or R-40, according to an embodiment.

FIG. 11 illustrates the thermal conductivity of various mixtures of R-134a and R-40. The thermal conductivities of the various mixtures were modeled using REFPROP v 9.1. The curved dotted and dashed line shows the thermal conductivity (in mW per m·K) of refrigerant mixtures of R134a and/or R-40 at 1 atm as a function of the mass fraction of R-40.

The curved dashed line shows the thermal conductivity of various refrigerant mixtures of R-134a and/or R-40 relative to the thermal conductivity of R-40. The other low GWP alternatives were also modeled in REFPROP v 9.1 in a refrigerant mixture with R-40. Each of the low GWP alternatives had a similar relationship with R-40 between the mass fraction of R-40 and the thermal conductivity of the refrigerant mixture as R134a. The thermal conductivity of a mixture of R134a and R-40 decreased as the mass fraction of R-40 increased.

The difference between the vertical dashed lines in FIG. 11 is approximately 5% and the difference between the horizontal dashed lines in FIG. 11 is approximately a mass fraction of 0.15. As shown by comparing the vertical dashed lines and horizontal dashed lines in FIG. 11, a detector (e.g., TCD 700) that is able to detect a 5% decrease in the thermal conductivity of a refrigerant would be able to detect when the refrigerant contains 15% or more of a contaminant (e.g., R-40) in an embodiment.

Detection Controlling System

Various TCD may be applied to an HVACR system controlling system. When a change of thermal conductivity of refrigerant is detected by the TCD, a controller 213 in communication with the TCD may generate an instruction to output an alarm or warning and send it to an output device 220 in communication with the controller 213 in FIG. 2. In response to the instructions, the output device 220 such as, but not limited to, a display or a speaker, may output a warning indicating the presence of a contaminant in the refrigerant gas used in the HVACR system. When the warning is outputted by the output device 220, the service personnel for the HVACR system would be directed to sample the refrigerant gas in the HVACR system or conduct some further procedures to determine what the source of the thermal conductivity change of the refrigerant gas used in the HVACR system is. Also, a portable device may be made with a controller integrated with the TCD so that a contamination detecting system could be applied to a remote unit, refrigerant cylinder or refrigerant reclaiming device by an operator to check the presence of contaminants.

The terminology used in this specification is intended to describe particular embodiments and is not intended to be limiting. The terms "a," "an," and "the" include the plural forms as well unless clearly indicated otherwise. The terms "comprise" and/or "comprising," when used in this specification, indicate the presence of the stated features, integers, steps, operations, elements, and/or components, but do not preclude the presence or addition of one or more other features, integers, steps, operations, elements, and/or components.

About the preceding description, it is to be understood that changes may be made in detail, especially in matters of the construction materials employed and the shape, size, and arrangement of parts without departing from the scope of the present disclosure. The word "embodiment" as used within this specification may, but does not necessarily, refer to the same embodiment. This specification and the embodiments described are exemplary only. Other and further embodiments may be devised without departing from the basic scope thereof, with the true scope and spirit of the disclosure being indicated by the claims that follow.

Aspects:

It is to be appreciated that any of aspects 1-21, 22-27. 28-33, 34-38, 39-43, 44-48, 49-74, 75-81, 82-87, 88-93, 94-96, 97-100 below may be combined with each other.

Aspect 1. A method of detecting contamination of refrigerant gas in a Heating, Ventilation, Air-conditioning and Refrigeration ("HVACR") system, comprising:
  detecting a property of refrigerant gas in a vapor space of the HVACR system by a detector;
  comparing the detected property with a reference property for the refrigerant gas in the vapor space; and
  determining that a contaminant is present in the refrigerant gas in the vapor space of the HVACR system if the detected property and the reference property is different from the reference property.

Aspect 2. The method of aspect 1, wherein if a difference between the detected property and the reference property is greater than a predetermined threshold, the detected property is determined as different from the reference property.

Aspect 3. The method of aspect 1 further comprising,
  in response to determining that a contaminant is present in the refrigerant gas in the vapor space, generating an instruction to output a warning and sending the instruction to an output device; and
  in response to receiving the instruction by the output device, outputting a warning that indicates the presence of contamination in the refrigerant gas of the vapor space.

Aspect 4. The method of aspect 1, wherein the vapor space is a refrigerant reservoir or a fluid line in a heat transfer circuit included in the HVACR system, or a refrigerant container in communication with the heat transfer circuit.

Aspect 5. The method of aspect 1, wherein the contaminant is methyl chloride ("R-40").

Aspect 6. The method of aspect 1, wherein the property of the refrigerant gas is a color of reagent included in the detector when the refrigerant gas from the vapor space in the HVACR system pass the reagent,
  the reference property for the refrigerant gas is a color of the reagent when an uncontaminated refrigerant gas to be used for the HVACR pass the reagent, and
  the reagent reacts with a contaminant and thereby has a change in the color thereof while the reagent does not react with the uncontaminated refrigerant gas.

Aspect 7. The method of aspect 6, wherein the reagent is sodium chromate or sodium permanganate.

Aspect 8. The method of aspect 6, wherein detecting a property of the refrigerant gas in a vapor space of the HVACR system by a detector includes:
  detecting a color of reagent included in the detector when the refrigerant gas from the vapor space in the HVACR system pass the reagent, and
  assessing a hue and value of the detected color of the reagent by an internal sensor included in the detector.

Aspect 9. The method of aspect 8, wherein comparing the detected property with a reference property for the refrigerant gas in the vapor space includes comparing the hue and value of the color of the reagent with the hue and value of reference colors by the internal sensor in the detector.

Aspect 10. The method of aspect 1, wherein the property of the refrigerant gas is the speed of sound through the refrigerant gas.

Aspect 11. The method of aspect 10, wherein detecting the speed of sound through refrigerant gas may include detecting a two-way travel time of the sound through the refrigerant gas of the vapor space of the HVACR system.

Aspect 12. The method of aspect 10, wherein the speed of sound through the refrigerant gas is given by a relationship $$v = \sqrt{\frac{\gamma RT}{M}},$$

in which v is the speed of sound through refrigerant gas, $\gamma$ is an adiabatic constant, R is a gas constant, M is a molecular weight of the refrigerant gas, and T is an absolute temperature.

Aspect 13. The method of aspect 10, further comprising:
calculating the molecular weight of the refrigerant gas using the detected speed of sound through the refrigerant gas; and
determining the amount ratio of the contaminant in the refrigerant gas using the calculated molecular weight.

Aspect 14. The method of aspect 1, wherein the property of the refrigerant gas is an impedance of a conductive material when the refrigerant gas contacts the conductive material, wherein the conductive material reacts with the contaminant and thereby has a change in the impedance thereof, and
the reference property is an impedance of the conductive material when an uncontaminated refrigerant gas to be used for the HVACR system contacts the conductive material.

Aspect 15. The method of aspect 14, wherein a constant current is applied to the conductive material while detecting the impedance of the conductive material.

Aspect 16. The method of aspect 14, wherein the contaminant is R-40, and the conductive material is zinc or magnesium.

Aspect 17. The method of aspect 1, wherein the property of the refrigerant gas is a thermal conductivity of the refrigerant gas in the vapor space of the HVACR system, and
the reference property is a thermal conductivity of an uncontaminated refrigerant gas to be used for the HVACR system.

Aspect 18. The method of aspect 17, further comprising:
while detecting the thermal conductivity of refrigerant gas in the vapor space, detecting the reference thermal conductivity.

Aspect 19. The method of aspect 17, wherein the detector is a Katharometer.

Aspect 20. The method of aspect 1, wherein the detector includes a circuit including a plurality of electrically heated filaments,
the property of refrigerant gas is a resistance of a first group of the electrically heated filaments disposed in a sample cell of the detector when the refrigerant gas passes the first group of the electrically heated filament, and
the reference property is a resistance of a second group of the electrically heated filaments disposed in a reference cell of the detector when an uncontaminated refrigerant gas to be used for the HVACR system passes the second group of the electrically heated filaments.

Aspect 21. The method of aspect 20, wherein the circuit is in a temperature-controlled cell.

Aspect 22. A method of detecting contamination of refrigerant gas in an HVACR system, comprising:
detecting a color of reagent included in the detector when the refrigerant gas from the vapor space in the HVACR system pass the reagent by a detector, wherein the reagent reacts with a contaminant and thereby has a change in the color there of while the reagent does not react with an uncontaminated refrigerant gas to be used for the HVACR system;
comparing the detected color of the reagent with a reference color of the reagent for the uncontaminated refrigerant gas; and
determining that a contaminant is present in the refrigerant gas in the HVACR system if the detected color of the reagent is different from the reference color of the reagent.

Aspect 23. The method of aspect 22, wherein detecting a color of reagent in the detector includes assessing a hue and value of the detected color of the reagent by an internal sensor included in the detector.

Aspect 24. The method of aspect 23, wherein comparing the detected color of the reagent with a reference color of the reagent for the uncontaminated refrigerant gas includes comparing the hue and value of the detected color of the reagent with the hue and value of the reference color by the internal sensor.

Aspect 25. The method of aspect 24, wherein if differences between the hue and value of the detected color and the hue and value of the reference color are greater than predetermined thresholds, the detected color is determined as different from the reference color.

Aspect 26. The method of aspect 22, wherein the reagent is sodium chromate or sodium permanganate.

Aspect 27. The method of aspect 22, wherein detecting a property of refrigerant gas in a vapor space of the HVACR system by a detector includes sensing the color of the refrigerant gas through a sight glass included in the detector.

Aspect 28. The method of aspect 27, wherein the reference color of the reagent is indicated on an indicator included in the detector.

Aspect 29. A method of detecting contamination of refrigerant gas in an HVACR system, comprising:
detecting the speed of sound through the refrigerant gas in a vapor space of the HVACR system by a detector;
comparing the detected speed of sound with a reference speed of sound for an uncontaminated refrigerant gas to be used for the HVACR system; and
determining that a contaminant is present in the refrigerant gas the vapor space if the detected speed of the sound is different from the reference speed of sound.

Aspect 30. The method of aspect 29, wherein if a difference between the detected speed of sound and the reference speed of sound is greater than a predetermined threshold, the detected speed of sound is determined as different from the reference speed of sound.

Aspect 31. The method of aspect 29, wherein the speed of sound through the refrigerant gas is given by a relationship $$v = \sqrt{\frac{\gamma RT}{M}}$$

in which v is the speed of sound through refrigerant gas, $\gamma$ is an adiabatic constant, R is a gas constant, M is a molecular weight of refrigerant gas, and T is an absolute temperature.

Aspect 32. The method of aspect 31, further comprising:
calculating the molecular weight of the refrigerant gas using the measured speed of sound through the refrigerant gas in the vapor space; and
determining the amount ratio of the contaminant in the refrigerant gas in the vapor space using the calculated molecular weight.

Aspect 34. The method of aspect 31, wherein detecting the speed of sound through the refrigerant gas in a vapor space includes detecting a two-way travel time of sound through the refrigerant gas of the vapor space using an ultrasonic interferometer.

Aspect 35. A method of detecting contamination of refrigerant gas in an HVACR system, comprising:
detecting an impedance of a conductive material in the refrigerant gas from a vapor space of the HVACR system by a detector, wherein the conductive material reacts to a contaminant in the refrigerant gas and thereby changes the impedance thereof while the conductive material does not react with an uncontaminated refrigerant gas to be used for the HVACR system;
comparing the detected impedance of the conductive material with a reference impedance of the conductive material when the uncontaminated refrigerant gas contacts the conductive material; and
determining that a contaminant is present in the refrigerant gas of the vapor space if the detected impedance is different from the reference.

Aspect 36. The method of aspect 35, wherein if a difference between the detected impedance and the reference impedance is greater than a predetermined threshold, the detected impedance is determined as different from the reference impedance.

Aspect 37. The method of aspect 35, wherein a constant current is applied to the conductive material.

Aspect 38. A method of detecting contamination of refrigerant gas in an HVACR system, comprising:
detecting a thermal conductivity of refrigerant gas in a vapor space of the HVACR system by a detector;
comparing the thermal conductivity of the refrigerant gas in the vapor space with a reference thermal conductivity of an uncontaminated refrigerant gas to be used for the HVACR system; and
determining that a contaminant is present in the refrigerant gas in the vapor space if the detected thermal conductive is different from the reference thermal conductivity.

Aspect 39. The method of aspect 38, wherein if a difference between the detected thermal conductivity and the reference thermal conductivity is greater than a predetermined threshold, the detected thermal conductivity is determined as different from the reference thermal conductivity.

Aspect 40. The method of aspect 38, wherein the detector is a Katharometer.

Aspect 41. A method of detecting contamination of refrigerant gas in an HVACR system, comprising:
detecting a resistance of a first group of electrically heated filaments disposed in a sample cell in a detector when the refrigerant gas in a vapor space of the HVACR system passes the electrically heated filament in the sample cell by the detector;
comparing the detected resistance with a reference resistance of a second group of electrically heated filaments disposed in a reference cell when an uncontaminated refrigerant gas to be used for the HVACR system passes the electrically heated filament in the reference cell; and
determining that contaminant is present in the refrigerant gas in the vapor space of the HVACR system if the detected resistance is different from the reference resistance.

Aspect 42. The method of aspect 41, further comprising: while detecting a resistance of a first group of electrically heated filaments, detecting a reference resistance of the second group of electrically heated filaments disposed in the reference cell.

Aspect 43. The method of aspect 41, wherein the detector includes the circuit in which the first and second groups of electrically heated filaments are included.

Aspect 44. The method of aspect 42, wherein the circuit is disposed in a temperature-controlled cell in the detector.

Aspect 45. A system for detecting contamination of refrigerant in an HVACR system, comprising:
a vapor space containing refrigerant gas; and
a detector, connected to the vapor space, detecting a property of the refrigerant gas in the vapor space, comparing the detected property with a reference property for uncontaminated refrigerant gas to be used for the HVACR system, and determining that a contaminant is present in the refrigerant gas of the vapor space if the detected property is different from the reference property.

Aspect 46. The system of aspect 45, wherein if a difference between the detected property and the reference property is greater than a predetermined threshold, the detected property is determined as different from the reference property.

Aspect 47. The system of aspect 45, further comprising:
a controller, in communication with the detector, receiving the determination that a contaminant is present in the refrigerant gas of the vapor space from the detector, and generating an instruction to output the warning that a contaminant is present in the vapor space; and
an output device, in communication with the controller, outputting the warning that a contaminant is present in the refrigerant gas of the vapor space, in response to receiving the instruction from the controller.

Aspect 48. The method of aspect 45, wherein the vapor space is a refrigerant reservoir or a fluid line included in a heat transfer circuit in the HVACR system, or a refrigerant container in communication with the heat transfer circuit.

Aspect 49. The method of aspect 45, wherein the detector includes a reagent that reacts with a contaminant and thereby has a change of color thereof while does not react to the uncontaminated refrigerant gas to be used for the HVACR system, and
the property of refrigerant gas is a color of the reagent when the refrigerant gas passes the reagent.

Aspect 50. The system of aspect 45, wherein the reagent is sodium chromate or sodium permanganate.

Aspect 51. The system of aspect 45, wherein the detector includes an internal sensor for assessing levels of hue and value of the detected color of the reagent, comparing the levels of hue and value of the detected color of the reagent with the levels of hue and value of a reference color of the reagent when an uncontaminated refrigerant gas to be used for the HVACR system passes the reagent, and determining that a contaminant is present in the refrigerant gas of the vapor space if the detected property is different from the reference property.

Aspect 52. The system of aspect 51, wherein if a difference between the levels of hue and value of the detected color of the reagent and the levels of hue and value of the reference color of the reagent is greater than a predetermined threshold, the detected color is determined as different from the reference color.

Aspect 53. The system of aspect 45, wherein the detector includes a sight glass through which the color change of the reagent is detected.

Aspect 54. The system of aspect 53, wherein the detector further includes an indicator indicating reference colors of the reagent for the uncontaminated refrigerant gas to be used for the HVACR system.

Aspect 55. The system of aspect 45, wherein the property of refrigerant gas is a speed of sound through the refrigerant gas in the vapor space of the HVACR system.

Aspect 56. The system of aspect 55, wherein the speed of sound through the refrigerant gas is given by a relationship $$v = \sqrt{\frac{\gamma RT}{M}}$$

in which v is the speed of sound through the refrigerant gas, γ is an adiabatic constant, R is a gas constant, M is a molecular weight of the refrigerant gas, and T is an absolute temperature.

Aspect 57. The system of aspect 55, wherein the detector includes a transducer outputting sound waves, a receiver receiving the sound waves which are transmitted or reflected, and a thermal sensor detecting a temperature of the refrigerant gas in the vapor space.

Aspect 58. The system of aspect 56, wherein the detector further detects a two-way travel time of sound through the refrigerant gas of the vapor space using an ultrasonic interferometer to obtain the speed of sound through the refrigerant gas in the vapor space.

Aspect 59. The system of aspect 56, wherein the detector calculate the molecular weight of the refrigerant gas using the measured speed of sound through the refrigerant gas in the vapor space and determine the amount ratio of a contaminant in the refrigerant gas in the vapor space using the calculated molecular weight.

Aspect 60. The system of aspect 45, wherein the detector includes a conductive material which reacts with a contaminant in the refrigerant gas in the vapor space and thereby has a change in the impedance thereof while does not react to the uncontaminated refrigerant gas to be used for the HVACR system, and
the property of the refrigerant gas is an impedance of the conductive material when the refrigerant gas in the vapor space of the HVACR system passes the conductive material.

Aspect 61. The system of aspect 60, wherein the detector applies a constant current to the conductive material.

Aspect 62. The system of aspect 60, wherein the contaminant is R-40, and the metal is zinc or magnesium.

Aspect 63. The system of aspect 60, wherein the conductive material has a shape of strip or wire.

Aspect 64. The system of aspect 45, wherein the property of the refrigerant gas is a thermal conductivity of the refrigerant gas in the vapor space.

Aspect 65. The system of aspect 64, wherein the detector is a Katharometer.

Aspect 66. The system of aspect 64, wherein the detector detects a difference between the thermal conductivity of the refrigerant gas in the vapor space and the reference conductivity of the uncontaminated refrigerant gas by detecting a change of voltage and resistance of the electrically heated filament.

Aspect 67. The system of aspect 64, wherein the detector includes a circuit including a plurality of electrically heated filaments.

Aspect 68. The system of aspect 67, wherein the circuit includes a first group of electrically heated filaments through which the refrigerant gas passes and and a second group of electrically heated filaments through which an uncontaminated refrigerant gas passes, and
the reference thermal conductivity for an uncontaminated refrigerant gas to be used for the HVACR system is obtained from the second group of electrically heated filaments.

Aspect 69. The system of aspect 67, wherein the circuit istemperature-controlled while the refrigerant gas passes the first group of filments.

Aspect 70. The system of aspect 67, wherein the detector generates a measurable voltage or resistance change when there is a difference between the thermal conductivity of the refrigerant gas passing the first group of electrically heated filaments and the reference thermal conductivity of the uncontaminated refrigerant gas passing the second group of electrically heated filaments.

Aspect 71. A system for detecting contamination of refrigerant gas in an HVACR system, comprising:
a vapor space containing refrigerant gas; and
a detector, which includes a reagent and is connected to the vapor space, detecting a color of the reagent when the refrigerant gas in the vapor space of the HVACR system passes the reagent, comparing the detected color of the reagent with a reference color of the reagent when an uncontaminated refrigerant gas to be used for the HVACR system, and determining that a contaminant is present in the refrigerant gas of the vapor space if the detected color of the reagent is different from a reference color of the reagent for an uncontaminated refrigerant gas to be used for the HVACR system,
wherein the reagent reacts with a contaminant and thereby changes the color thereof while does not react to the uncontaminated refrigerant gas.

Aspect 72. The system of aspect 71, wherein the detector includes an internal sensor,
the internal sensor assesses a hue and value of the detected color of the reagent, compares the levels of hue and value of the detected color with the levels of hue and value of the reference, and determines that a contaminant is present in the refrigerant gas of the vapor space if the levels of hue and value of the detected color are different from the levels of hue and value of the reference color.

Aspect 73. The system of aspect 72, wherein if differences between the levels of hue and value the detected color and the levels of hue and value of the reference color are greater than predetermined thresholds, the detected color is determined as different from the reference color.

Aspect 74. The system of aspect 71, further comprising:
a controller, in communication with the detector, receiving from the detector the determination that a contaminant is present in the refrigerant gas of the vapor space and generating an instruction to output a warning that a contaminant is present in the refrigerant gas of the vapor space; and
an output device, in communication with the controller, receiving from the controller the instruction and outputting the warning.

Aspect 75. The method of aspect 71, wherein the vapor space is a refrigerant reservoir or a fluid line included in a heat transfer circuit in the HVACR system, or a refrigerant container in communication with the heat transfer circuit.

Aspect 76. The method of aspect 71, wherein the contaminant is R-40.

Aspect 77. The system of aspect 71, wherein the reagent is sodium chromate or sodium permanganate.

Aspect 78. The system of aspect 71, wherein the detector includes a sight glass through which the color change of the reagent may be observed.

Aspect 79. The system of aspect 78, wherein the detector further includes an indicator that indicates a reference color of the reagent for the uncontaminated refrigerant gas to be used for the HVACR system.

Aspect 80. A system for detecting contamination of refrigerant gas in an HVACR system, comprising:
a vapor space containing refrigerant gas; and
a detector, connected to the vapor space, detecting a speed of sound through the refrigerant gas in the vapor space, comparing the detected speed of sound with a reference speed of sound through uncontaminated refrigerant gas to be used for the HVACR system, and determining that a contaminant is present in the refrigerant gas of the vapor space if the detected speed of sound is different from the reference speed of sound difference.

Aspect 81. The system of aspect 80, wherein if a difference between the detected speed of sound and the reference speed of sound is greater than a predetermined threshold, the detected speed of sound is determined as different from the reference speed of sound.

Aspect 82. The system of aspect 80, further comprising:
a controller, in communication with the detector, receiving from the detector the determination that a contaminant is present in the refrigerant gas of the vapor space and generating an instruction to output an warning that a contaminant is present in the refrigerant gas of the vapor space; and
an output device, in communication with the controller, outputting the warning in response to receiving the instruction from the controller.

Aspect 83. The system of aspect 80, wherein the speed of sound through the refrigerant gas is given by a relationship $$v = \sqrt{\frac{\gamma RT}{M}}$$

which v is the speed of sound through refrigerant gas, γ is an adiabatic constant, R is a gas constant, M is a molecular weight of refrigerant gas, and T is an absolute temperature.

Aspect 84. The system of aspect 83, wherein the detector detects a two-way travel time of sound through the refrigerant gas of the vapor space to obtain the speed of sound through the refrigerant gas.

Aspect 85. The system of aspect 83, wherein the detector calculates the molecular weight of the refrigerant gas in the vapor space using the detected speed of sound through refrigerant gas and determines the amount ratio of a contaminant in the refrigerant gas using the calculated molecular weight.

Aspect 86. The system of aspect 80, wherein the detector is an ultrasonic interferometer.

Aspect 87. A system for detecting contamination of refrigerant gas in an HVACR system, comprising:
a vapor space containing refrigerant gas; and
a detector, which includes a conductive material and is connected to the vapor space, detecting an impedance of the conductive material when the refrigerant gas in the vapor space contacts the conductive material, comparing the detected impedance with a reference impedance of the conductive material when an uncontaminated refrigerant gas contacts the conductive material and determining that a contaminant is present in the refrigerant gas of the vapor space if the detected impedance is different from the reference impedance,
wherein the conductive material reacts to a contaminant and thereby has a change in the impedance thereof while does not react to the uncontaminated refrigerant gas to be used for the HVACR system.

Aspect 88. The system of aspect 87, wherein if a difference between the detected impedance and the reference impedance is greater than a predetermined threshold, the detected impedance is determined as different from the reference impedance.

Aspect 89. The system of aspect 87, further comprising:
a controller, in communication with the detector, receiving from the detector the determination that a contaminant is present in the refrigerant gas of the vapor space and generating an instruction to output an warning that a contaminant is present in the refrigerant gas of the vapor space; and
an output device, in communication with the controller, outputting the warning in response to receiving the instruction from the controller.

Aspect 90. The system of aspect 87, wherein the detector applies a constant current to the conductive material.

Aspect 91. The system of aspect 87, wherein the contaminant is R-40, and the conductive material is zinc or magnesium.

Aspect 92. The system of aspect 87, wherein the conductive material has a shape of strip or wire.

Aspect 93. A system for detecting contamination of refrigerant gas in an HVACR system, comprising:
a vapor space containing refrigerant gas; and
a detector, connected to the vapor space, including a first group of electronically heated filaments through which the refrigerant gas from the vapor space passes and a second group of electronically heated filaments through which an uncontaminated refrigerant gas to be used for the HVACR system passes,
wherein when the detector detects a difference between a thermal conductivity of the refrigerant gas from the vapor space and a reference thermal conductivity of the uncontaminated refrigerant gas, compares the detected thermal conductivity of the refrigerant gas with the reference thermal conductivity, and determines that a contaminant is present in the refrigerant of the vapor space if the detected thermal conductivity of the refrigerant gas is different from the reference thermal conductivity, the detector determines that a contaminant is present in the refrigerant gas from the component.

Aspect 94. The system of aspect 93, wherein if a difference between the detected thermal conductivity of the refrigerant gas and the thermal conductivity of the uncontaminated refrigerant gas to be used for the HVACR system is greater than a predetermined threshold, the refrigerant gas is determined as different from the uncontaminated refrigerant gas to be used for the HVACR system.

Aspect 95. The system of aspect 93, further comprising:
a controller, in communication with the detector, receiving from the detector the determination that a contaminant is present in the refrigerant gas of the vapor space and generating an instruction to output an warning that a contaminant is present in the refrigerant gas of the vapor space; and
an output device, in communication with the controller, outputting the warning in response to receiving the instruction from the controller.

Aspect 96. The system of aspect 93, wherein the detector is a Katharometer.

Aspect 97. A system for detecting contamination of refrigerant gas in an HVACR system, comprising:
a vapor space containing refrigerant gas; and
a detector, connected to the vapor space, including a circuit that includes a plurality of electrically heated filaments disposed in a temperature-controlled cell,
wherein the circuit detects a resistance of a first group of electrically heated filaments when the refrigerant gas from the vapor space passes the first group of the electrically heated filaments and a reference resistance of a second group of electrically heated filaments when an uncontaminated refrigerant gas to be used for the HVACR system, compares the detected resistance of the first group of the electrically heated filaments with the reference resistance, and generates a measurable voltage change if the detected resistance of the first group of the electrically heated filaments is different from the reference resistance, and in response to detecting the measurable voltage change, the detector determines that a contaminant is present in the refrigerant gas from the vapor space.

Aspect 98. The system of aspect 97, wherein if a difference between the detected resistance of the first group of the electrically heated filaments and the reference resistance is greater than a predetermined threshold, the detected resistance of the first group of the electrically heated filaments is determined as different from the reference resistance.

What is claimed is:

1. A system for detecting contamination of refrigerant in an HVACR system, comprising:
    a vapor space containing refrigerant gas, the vapor space being a fluid line included in a heat transfer circuit in the HVACR system; and
    a detector, connected to the vapor space, detecting a speed of sound through the refrigerant gas in the vapor space to obtain a detected speed of sound, comparing the detected speed of sound with a reference speed of sound for uncontaminated refrigerant gas, and determining that a gaseous contaminant is present in the refrigerant gas of the vapor space when the detected speed of sound is different from the reference speed of sound, wherein
    the detector includes:
        a transducer outputting sound waves, and
        the receiver receiving the sound waves after being reflected off a back surface of the vapor space, the receiver spaced being apart from the transducer, and
    the detector measures a two-way travel time of the sound waves through the vapor space from the transducer to the receiver.

2. The system of claim 1, wherein the detected speed of sound is determined as different from the reference speed of sound when a difference between the detected speed of sound and the reference speed of sound is greater than a predetermined threshold.

3. The system of claim 1, further comprising:
    a controller, in communication with the detector, receiving the determination that a gaseous contaminant is present in the refrigerant gas of the vapor space from the detector, and generating an instruction to output a warning that a gaseous contaminant is present in the vapor space; and
    an output device, in communication with the controller, outputting the warning that a gaseous contaminant is present in the refrigerant gas of the vapor space, in response to receiving the instruction from the controller.

4. The system of claim 1, wherein
the speed of sound through the refrigerant gas is given by a relationship $$v = \sqrt{\frac{\gamma RT}{M}},$$

in which v is the speed of sound through the refrigerant gas, $\gamma$ is an adiabatic constant, R is a gas constant, M is a molecular weight of the refrigerant gas, and T is an absolute temperature.

5. The system of claim 4, wherein the detector calculates the molecular weight of the refrigerant gas using the detected speed of sound through the refrigerant gas in the vapor space and determines a ratio of a gaseous contaminant in the refrigerant gas in the vapor space using the calculated molecular weight.

6. The system of claim 1, wherein the detector includes a thermal sensor detecting a temperature of the refrigerant gas in the vapor space.

7. The system of claim 1, wherein the gaseous contaminant is methyl chloride ("R-40").

8. The system of claim 1, wherein the refrigerant gas is at least one selected from the group consisting of R-134a, R-1234yf, R-1234ze(E), R-513A, and R-516A.

9. The system of claim 1, wherein the transducer and receiver are outside of the vapor space.

10. A method of detecting contamination of refrigerant gas in a HVACR system, comprising:
    detecting a speed of sound through refrigerant gas in a vapor space of the HVACR system by a detector to obtain a detected speed of sound, the vapor space being a fluid line included in a heat transfer circuit in the HVACR system, the detector including a transducer outputting sound waves and a receiver receiving the sound waves after being reflected off a back surface of the vapor space, the receiver spaced being apart from the transducer, wherein detecting the speed of sound through the refrigerant gas includes measuring a two-way travel time of the sound waves through the vapor space from the transducer to the receiver;
    comparing the detected speed of sound with a reference speed of sound for uncontaminated refrigerant gas; and
    determining that a gaseous contaminant is present in the refrigerant gas in the vapor space of the HVACR system when the detected speed of sound is different from the reference speed of sound.

11. The method of claim 10, wherein the detected speed of sound is determined as different from the reference speed of sound when a difference between the detected speed of sound and the reference speed of sound is greater than a predetermined threshold.

12. The method of claim 10, wherein
the speed of sound through the refrigerant gas is given by a relationship $$v = \sqrt{\frac{\gamma RT}{M}},$$

in which v is the speed of sound through the refrigerant gas, $\gamma$ is an adiabatic constant, R is a gas constant, M is a molecular weight of the refrigerant gas, and T is an absolute temperature.

13. The method of claim 10, wherein the gaseous contaminant is methyl chloride ("R-40").

14. The method of claim 10, wherein the refrigerant gas is at least one selected from the group consisting of R-134a, R-1234yf, R-1234ze(E), R-513A, and R-516A.

15. The method of claim 10, wherein the transducer and receiver are outside of the vapor space.

* * * * *